United States Patent
Matsushita

(10) Patent No.: US 9,326,920 B2
(45) Date of Patent: May 3, 2016

(54) ULTRAVIOLET-SHIELDING AGENT, METHOD FOR PRODUCING THE SAME, ULTRAVIOLET-SHIELDING AGENT-CONTAINING DISPERSION LIQUID, AND COSMETIC PREPARATION

(75) Inventor: Hirokazu Matsushita, Tokyo (JP)

(73) Assignee: SUMITOMO OSAKA CEMENT CO., LTD. (JP)

( * ) Notice: Subject to any disclaimer, the term of this patent is extended or adjusted under 35 U.S.C. 154(b) by 0 days.

(21) Appl. No.: 14/117,751

(22) PCT Filed: May 18, 2012

(86) PCT No.: PCT/JP2012/062812
§ 371 (c)(1),
(2), (4) Date: Nov. 14, 2013

(87) PCT Pub. No.: WO2012/157757
PCT Pub. Date: Nov. 22, 2012

(65) Prior Publication Data
US 2014/0086966 A1    Mar. 27, 2014

(30) Foreign Application Priority Data

| May 18, 2011 | (JP) | 2011-111381 |
| May 18, 2011 | (JP) | 2011-111383 |
| Mar. 30, 2012 | (JP) | 2012-081062 |
| Mar. 30, 2012 | (JP) | 2012-081063 |

(51) Int. Cl.
A61K 8/02 (2006.01)
A61K 8/27 (2006.01)
(Continued)

(52) U.S. Cl.
CPC ............ *A61K 8/0241* (2013.01); *A61K 8/0266* (2013.01); *A61K 8/27* (2013.01); *A61K 8/28* (2013.01); *A61K 8/29* (2013.01); *A61K 8/35* (2013.01); *A61K 8/36* (2013.01); *A61K 8/368* (2013.01); *A61K 8/411* (2013.01); *A61K 8/8147* (2013.01); *A61Q 17/04* (2013.01); *C08F 2/18* (2013.01); *C08F 2/22* (2013.01); *C08F 2/44* (2013.01); *A61K 2800/412* (2013.01); *A61K 2800/621* (2013.01); *A61K 2800/622* (2013.01)

(58) Field of Classification Search
None
See application file for complete search history.

(56) References Cited

U.S. PATENT DOCUMENTS 6,200,680 B1 * 3/2001 Takeda et al. ............. 428/402
2011/0110994 A1   5/2011 Inokuchi et al.

FOREIGN PATENT DOCUMENTS

| JP | A-03-200721 | 9/1991 |
| JP | A-07-291837 | 11/1995 |

(Continued)

OTHER PUBLICATIONS

Machine translation, WO 2010/098249 (2010).*
(Continued)

*Primary Examiner* — Bethany Barham
*Assistant Examiner* — Barbara Frazier
(74) *Attorney, Agent, or Firm* — Merchant & Gould P.C.

(57) ABSTRACT

The invention provides an ultraviolet-shielding agent including resin particles formed by coating a core portion with a coating layer, wherein the core portion is made of any one resin of an organic ultraviolet absorbent-containing resin and an inorganic particle-containing resin, and the coating layer is made of the other resin or both resins, a method for producing the same, an ultraviolet-shielding agent-containing dispersion liquid, and a cosmetic preparation.

16 Claims, 12 Drawing Sheets

(51) Int. Cl.

| | | |
|---|---|---|
| *A61K 8/28* | (2006.01) | |
| *A61K 8/29* | (2006.01) | |
| *A61K 8/35* | (2006.01) | |
| *A61K 8/36* | (2006.01) | |
| *A61K 8/368* | (2006.01) | |
| *A61K 8/41* | (2006.01) | |
| *A61K 8/81* | (2006.01) | |
| *A61Q 17/04* | (2006.01) | |
| *C08F 2/18* | (2006.01) | |
| *C08F 2/22* | (2006.01) | |
| *C08F 2/44* | (2006.01) | |

(56) References Cited

FOREIGN PATENT DOCUMENTS

| JP | A-2001-315258 | 11/2001 | |
| JP | A-2003-506545 | 2/2003 | |
| JP | A-2003-506546 | 2/2003 | |
| JP | 2004-182984 * | 7/2004 | ............... C09K 3/00 |
| JP | A-2009-299059 | 12/2009 | |
| WO | WO 01/10936 A1 | 2/2001 | |
| WO | WO 01/10937 A1 | 2/2001 | |
| WO | WO 2010/098249 A1 | 9/2010 | |
| WO | WO 2011/034032 A1 | 3/2011 | |

OTHER PUBLICATIONS

International Search Report for International Patent Application No. PCT/JP2012/062812 (mailed Aug. 7, 2012).

European Search Report for European Patent Application No. 12785606.0 (mailed Oct. 22, 2014).

Office Action for Japanese Patent Application No. 2012-114498 (mailed Dec. 1, 2015).

Office Action for Japanese Patent Application No. 2012-114499 (mailed Dec. 1, 2015).

\* cited by examiner

ULTRAVIOLET-SHIELDING AGENT, METHOD FOR PRODUCING THE SAME, ULTRAVIOLET-SHIELDING AGENT-CONTAINING DISPERSION LIQUID, AND COSMETIC PREPARATION

This application is a U.S. National Stage Application under 35 U.S.C. §371 of International Patent Application No. PCT/JP2012/062812 filed 18 May 2012, which claims the benefit of priority to Japanese Patent Application No. 2011-111381 filed 18 May 2011, Japanese Patent Application No. 2011-111383 filed 18 May 2011, Japanese Patent Application No. 2012-081062 filed 30 Mar. 2012 and Japanese Patent Application No. 2012-081063 filed 30 Mar. 2012, the disclosures of all of which are hereby incorporated by reference in their entireties. The International Application was published in Japanese on 22 Nov. 2012 as WO 2012/157757.

TECHNICAL FIELD

The present invention relates to an ultraviolet-shielding agent, a method for producing the same, an ultraviolet-shielding agent-containing dispersion liquid, and a cosmetic preparation, and more specifically to an ultraviolet-shielding agent preferable for use in a variety of cosmetics, such as skin care cosmetics, makeup cosmetics and body care cosmetics, particularly, for cosmetic preparations which require an ultraviolet-shielding function, such as whitening cosmetics which are skin care cosmetics, base makeup cosmetics, and sunscreen cosmetics which are body care cosmetics, an ultraviolet-shielding agent-containing dispersion liquid which contains the ultraviolet-shielding agent, and a cosmetic preparation.

BACKGROUND

Conventionally, as an ultraviolet-shielding agent used for cosmetics, inorganic ultraviolet-shielding agents and organic ultraviolet absorbents have been selectively used depending on use. Since different kinds of inorganic ultraviolet-shielding agents and organic ultraviolet absorbents can shield different wavelengths of ultraviolet rays, cosmetic preparations have been formulated by appropriately combining inorganic ultraviolet-shielding agents and organic ultraviolet-shielding agents.

Particularly, since inorganic ultraviolet-shielding agents scatter or reflect ultraviolet rays using physical mechanisms, inorganic ultraviolet-shielding agents have a small influence on skin, and are used in sun-screening for a wide range of users from infants to adults.

Preferable examples of the inorganic ultraviolet-shielding agents include zinc oxide, titanium oxide and the like which have a high opacifying power with respect to ultraviolet rays and are also used as white dyes.

However, in a case in which zinc oxide or titanium oxide was applied to cosmetic preparations, when the average dispersed particle diameter was 0.1 µm or more, there were problems in that cosmetic preparations were whitened so as to degrade transparency, and natural makeup could not be obtained.

In addition, it is difficult to disperse zinc oxide or titanium oxide in cosmetic preparations in an average dispersed particle diameter of 0.1 µm or less. In addition, even when zinc oxide or titanium oxide could be dispersed, such zinc oxide or titanium oxide had a high surface activity, and provided a rough feeling when coming into contact with skin. In addition, in a case in which the primary particle diameter or average dispersed particle diameter in cosmetic preparations of zinc oxide or titanium oxide was large, there was a problem in that the transparency of cosmetic preparations was degraded.

Meanwhile, organic ultraviolet absorbents chemically absorb energy, and convert the energy into thermal energy, thereby preventing ultraviolet rays from intruding into skin cells. In addition, when compared with inorganic ultraviolet-shielding agents, organic ultraviolet absorbents produce a high ultraviolet-shielding effect even in a small amount, and are used for adult sun-screening. Compared with inorganic ultraviolet-shielding agents, organic ultraviolet absorbents do not become white when coated on skin and have an advantage of a high transparency.

Examples of the organic ultraviolet absorbents include dibenzoylmethane-based compounds, benzophenone derivatives, para-aminobenzoic acid derivatives, methoxycinnamic acid derivatives, salicylic acid derivatives and the like, and, in particular, as a UVA absorbent that absorbs near ultraviolet rays, a dibenzoylmethane-based compound, particularly, 4-tert-butyl-4'-methoxydibenzoylmethane (avobenzone) is widely used.

However, since organic ultraviolet absorbents are insoluble in water, it was necessary to dissolve an organic ultraviolet absorbent in a specific non-aqueous solvent in order to exhibit the ultraviolet absorbing effect, and therefore limited kinds of solvents could be used, which created a problem of a decrease in the degree of freedom as cosmetic preparations. Furthermore, when a non-aqueous solvent was mixed with a cosmetic preparation, there was a problem of the occurrence of a sticky feeling.

Furthermore, when an inorganic ultraviolet-shielding agent and an organic ultraviolet absorbent are jointly used, there is a concern that the organic ultraviolet absorbent may be recrystallized due to the influence of metallic ions included in the inorganic ultraviolet-shielding agent such that the qualities or colors of cosmetic preparations may be changed, and the feeling of use of cosmetic preparations may degrade. As described above, there was a problem in that an inorganic ultraviolet-shielding agent and an organic ultraviolet absorbent could not be freely mixed when formulating a cosmetic preparation.

Therefore, in order to solve the above problems, resin powder, which is highly transparent, excellent in terms of feeling in use, and has an average particle diameter of 0.1 µm to 1 µm, obtained by including metallic oxide particles having an ultraviolet-shielding function in an acryl-based resin is proposed (PTL 1).

In the resin powder, since direct contact between the organic ultraviolet absorbent and the metallic oxide is prevented, the recrystallization and the like of the organic ultraviolet absorbent are suppressed.

In addition, as resin powder that suppresses the dermal irritancy of an organic ultraviolet absorbent, resin powder including a core portion made of a (meth)acryl-based resin containing an organic ultraviolet absorbent, which is formed by dispersing a monomer that forms the (meth)acryl-based resin in which the organic ultraviolet absorbent is dissolved in an aqueous medium and causing a polymerization reaction, and a surface layer portion made of a (meth)acryl-based resin which is formed on a surface of the core portion and does not contain the organic ultraviolet absorbent is proposed (PTL 2).

In the resin powder, since direct contact between the organic ultraviolet absorbent and a metallic oxide is prevented, the recrystallization and the like of the organic ultraviolet absorbent are suppressed.

CITATION LIST

Patent Literature

[PTL 1] Domestic Republication of PCT International Application WO2011/34032
[PTL 2] Japanese Laid-open Patent Publication No. 07-291837

SUMMARY OF INVENTION

Technical Problem

However, even for sunscreen agents in which resin particles including a metallic oxide as described in PTL 1 and an organic ultraviolet absorbent are jointly used, there was a problem in that UVA waves (particularly 380 nm to 400 nm) which serve as a cause of photoaging could not be sufficiently shielded.

In addition, for sunscreen agents in which resin particles including an organic ultraviolet absorbent as described in PTL 2 and a metallic oxide are jointly used, there was a problem in that UVA waves (particularly 380 nm to 400 nm) which serve as a cause of photoaging could not be sufficiently shielded.

The invention has been made in consideration of the above circumstances, and an object of the invention is to provide an ultraviolet-shielding agent which has a strong ultraviolet-shielding effect and can be mixed not only with water-in-oil (W/O) cosmetic preparations but also with oil-in-water (O/W) cosmetic preparations, a method for producing the same, an ultraviolet-shielding agent-containing dispersion liquid, and a cosmetic preparation.

Solution to Problem

As a result of repeating thorough studies in order to solve the above problems, the present inventors and the like found that, when resin particles formed by coating a core portion made of any one resin of an organic ultraviolet absorbent-containing resin and an inorganic particle-containing resin with a coating layer made of the other resin or both resins are included, the ultraviolet-shielding effect is enhanced, and an ultraviolet-shielding agent can be applied to the formulation of oil-in-water (O/W) aqueous cosmetic preparations, and completed the invention.

That is, ultraviolet-shielding agents of the invention are as follows.

(1) An ultraviolet-shielding agent including resin particles formed by coating a core portion with a coating layer, wherein the core portion is made of any one resin of an organic ultraviolet absorbent-containing resin and an inorganic particle-containing resin, and the coating layer is made of the other resin or both resins.

(2) The ultraviolet-shielding agent according to the above (1), in which the core portion is made of the inorganic particle-containing resin, and the coating layer is made of the organic ultraviolet absorbent-containing resin.

(3) The ultraviolet-shielding agent according to the above (1) or (2), in which a refractive index of the inorganic particles is 1.9 or more.

(4) The ultraviolet-shielding agent according to any one of the above (1) to (3), in which the inorganic particles are metallic oxide particles.

(5) The ultraviolet-shielding agent according to any one of the above (1) to (4), in which the organic ultraviolet absorbent is at least one selected from the group consisting of dibenzoylmethane-based compounds, benzophenone derivatives, para-aminobenzoic acid derivatives, methoxycinnamic acid derivatives and salicylic acid derivatives.

(6) The ultraviolet-shielding agent according to any one of the above (1) to (5), in which an average particle diameter of the resin particles is 0.1 µm to 5 µm.

(7) The ultraviolet-shielding agent according to any one of the above (1) to (6), in which the core portion is made of an inorganic particle-containing resin, and has a spherical shape with an average particle diameter of 0.05 µm to 5.0 µm.

(8) The ultraviolet-shielding agent according to the above (7), in which the core portion has a spherical shape with an average particle diameter of 0.05 µm to 4.8 µm.

(9) The ultraviolet-shielding agent according to any one of the above (1) to (8), in which the core portion is made of an organic ultraviolet absorbent-containing resin, and has a spherical shape with an average particle diameter of 0.05 µm to 5.0 µm.

(10) The ultraviolet-shielding agent according to any one of the above (1) to (9), in which an average primary particle diameter of the inorganic particles is 0.003 µm to 0.1 µm.

(11) The ultraviolet-shielding agent according to any one of the above (1) to (10), in which a thickness of the coating layer is 0.01 µm to 0.5 µm.

(12) The ultraviolet-shielding agent according to any one of the above (1) to (11), in which a content rate of the organic ultraviolet absorbent in the organic ultraviolet absorbent-containing resin is 0.1% by mass to 80% by mass.

(13) The ultraviolet-shielding agent according to any one of the above (1) to (12), in which a content rate of the inorganic particles in the inorganic particle-containing resin is 1% by mass to 80% by mass.

(14) The ultraviolet-shielding agent according to any one of the above (1) to (13), in which a mass ratio (Mv:Mm) of the ultraviolet absorbent to the inorganic particles is 1:9 to 5:5.

(15) An ultraviolet-shielding agent-containing dispersion liquid formed by dispersing the ultraviolet-shielding agent as defined in one of the above (1) to (14) in a dispersion medium.

(16) A cosmetic preparation containing any one or both of the ultraviolet-shielding agent as defined in any one of the above (1) to (14) and the ultraviolet-shielding agent-containing dispersion liquid as defined in the above (15).

(17) A method for producing ultraviolet-shielding agents including:

a step of obtaining a resin monomer-dispersed liquid by dispersing inorganic particles in a resin monomer including a dispersant, a step of obtaining a resin monomer-dissolved liquid by dissolving an organic ultraviolet absorbent and a dispersant in the resin monomer, a step of obtaining a dispersion liquid containing a core portion made of an organic ultraviolet absorbent-containing resin or an inorganic particle-containing resin by suspending or emulsifying the resin monomer-dispersed liquid or the resin monomer-dissolved liquid in pure water including a suspension protectant, a silicone-based defoamer and a crosslinking agent, and then adding a polymerization initiator so as to carry out suspension polymerization or emulsification polymerization, thereby, a step of obtaining a coating resin by suspending or emulsifying the resin monomer-dispersed liquid or the resin monomer-dissolved liquid in pure water containing a polymerization initiator, and a step of obtaining an ultraviolet-shielding agent including resin particles having a core shell structure by mixing the coating resin and the dispersion liquid containing the core portion so as to carry out suspension polymerization or emulsification polymerization.

Advantageous Effects of Invention

Since the ultraviolet-shielding agent of the invention includes the resin particles formed by coating the core portion made of any one resin of an organic ultraviolet absorbent-containing resin and an inorganic particle-containing resin with the coating layer made of the other resin or both resins, it is possible to shield ultraviolet rays having a wavelength of 380 nm to 400 nm, which could not be shielded in the past, and to enhance the ultraviolet-shielding effect.

In addition, since there is no concern that the organic ultraviolet absorbent and the inorganic particles come into direct contact with each other, it is possible to prevent disadvantages in which the organic ultraviolet absorbent is crystallized due to the influence of metallic ions caused by the inorganic particles in the presence of ultraviolet rays such that the qualities or colors of cosmetic preparations are changed and the feelings of cosmetic preparations in use degrade, to enhance photostability, and to stabilize the qualities of cosmetic preparations.

In addition, since it is not necessary to dissolve the organic ultraviolet absorbent in a specific non-aqueous solvent, it is possible to apply the agent not only to water-in-oil (W/O) cosmetic water but also to oil-in-water (O/W) cosmetic water, for which it was difficult to formulate the agent in the past, and aqueous cosmetic preparations, such as sunscreen gels, and to improve the degree of freedom of the formulation as cosmetic preparations.

According to the method for producing ultraviolet-shielding agents of the invention, it is possible to produce ultraviolet-shielding agents including resin particles formed by coating a core portion made of any one resin of an organic ultraviolet absorbent-containing resin and an inorganic particle-containing resin with a coating layer made of the other resin or both resins in a favorable yield using a simple apparatus, and to reduce production costs.

DESCRIPTION OF EMBODIMENTS

Figure 1:
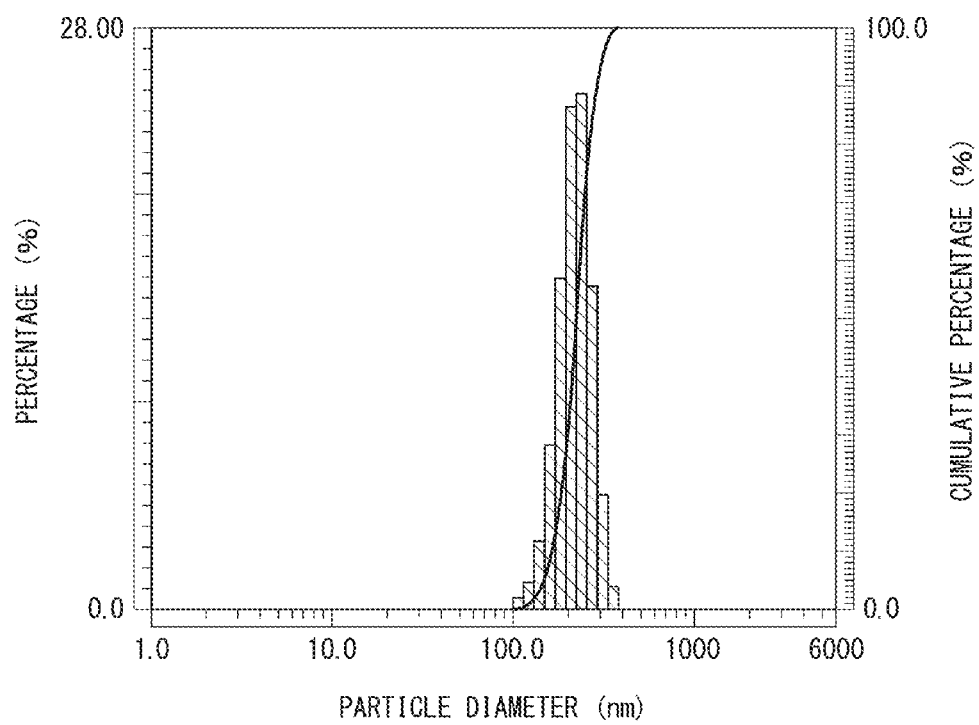
FIG. 1 is a view illustrating the volume particle size distribution and cumulative volume particle size distribution of a dispersion liquid of core resin particles D5 of Example 1 of the invention.

Embodiments for carrying out the ultraviolet-shielding agent, ultraviolet-shielding agent-containing dispersion liquid and cosmetic preparation of the invention will be described.

Meanwhile, the following embodiments are to specifically describe the invention in order for easier understanding of the purport of the invention, and do not limit the invention unless particularly otherwise described.

[Ultraviolet-Shielding Agent]

An ultraviolet-shielding agent of the present embodiment includes resin particles formed by coating a core portion with a coating layer, wherein the coating layer is made of any one resin of an organic ultraviolet absorbent-containing resin and an inorganic particle-containing resin, and the coating layer is made of the other resin or both resins.

The resin particles are formed by coating a core portion made of any one resin of an organic ultraviolet absorbent-containing resin and an inorganic particle-containing resin with a coating layer made of the other resin (hereinafter, may also be referred to as a core shell structure or a core shell type).

In addition, the resin particles may have a double-coated structure obtained by partially or fully coating resin particles having a core shell structure with a coating layer made of any one of an ultraviolet absorbent-containing resin and an inorganic particle-containing resin.

Furthermore, the resin particles may have a three or more layer-coated structure obtained by stacking coating layers made of any one or both of an ultraviolet absorbent-containing resin and an inorganic particle-containing resin.

Among the above structures, the structure obtained by partially or fully coating a core portion made of any one resin of an ultraviolet absorbent-containing resin and an inorganic particle-containing resin with a coating layer made of the other resin or both resins (core shell structure) is preferable.

The core shell structure and structures obtained by repeatedly coating the core shell structure efficiently exert an absorption effect of the organic ultraviolet absorbent and a scattering and reflection effect of the inorganic particles, thereby easily obtaining a synergetic effect.

The average particle diameter of the resin particles is preferably 0.1 μm to 5 μm, and more preferably 0.1 μm to 1 μm.

Here, the average particle diameter of the resin particles refers to the particle diameter at the 50 volume % point (D50)

in a cumulative volume particle size distribution obtained by measuring the diameters of dispersed particles in a dispersion liquid, in which the ultraviolet-shielding agent of the embodiment, polyether-denatured silicone SH3775 (manufactured by Dow Corning Toray Co., Ltd.) and decamethylcyclopentasiloxane SH245 (manufactured by Dow Corning Toray Co., Ltd.) have been rotated 2500 times so as to be mixed and dispersed over 3 hours using a sand mill so that the ultraviolet-shielding agent, polyether-denatured silicone and decamethylcyclopentasiloxane SH245 respectively account for 5% by mass, 10% by mass and 85% by mass, using a dynamic light scattering particle size distribution measurement apparatus LB-550 (manufactured by Horiba, Ltd.).

The average particle diameter of the resin particles obtained in the above manner, that is, the diameter of the dispersed particles (D50) approximately matched the primary particle diameter (the average diameter at the longest linear portion of the resin particles) of the resin particles when the resin particles are observed using a scanning electron microscope (SEM). Therefore, it is considered that the resin particles do not aggregate in the dispersion liquid.

In a case in which the average particle diameter of the resin particles is less than 0.1 it becomes difficult to uniformly disperse the inorganic particles in the resin, which is not preferable, and, on the other hand, in a case in which the average particle diameter exceeds 5 μm, transparency is degraded when the resin particles are mixed with a cosmetic preparation or the like, which is not preferable.

The average particle diameter in the core portion is preferably 0.05 μm to 5.0.

Here, in a case in which the average particle diameter in the core portion is less than 0.05 μm, there are cases in which the ultraviolet-shielding effect becomes insufficient, which is not preferable, and, on the other hand, in a case in which the average particle diameter exceeds 5.0 μm, the thickness of the coating layer becomes relatively thin, and, consequently, there are cases in which the ultraviolet-shielding effect in the coating layer is not sufficiently exhibited, which is not preferable.

In addition, the thickness of the coating layer is preferably 0.01 μm to 0.5 μm, and more preferably 0.01 μm to 0.2 μm.

Here, in a case in which the thickness of the coating layer is less than 0.01 μm, the effect of the coating layer for covering the core portion becomes insufficient, and there are cases in which the ultraviolet-shielding effect in the coating layer is not sufficiently exhibited, which is not preferable, and, in a case in which the thickness of the coating layer exceeds 0.5 μm, the coating layer becomes too thick such that the average particle diameter in the core portion becomes relatively small, and, consequently, there are cases in which the ultraviolet scattering and reflection effect or ultraviolet absorption effect of the core portion cannot be sufficiently exhibited, which is not preferable.

The ratio (Mv:Mm) of the mass (Mv) of the ultraviolet absorbent to the mass (Mm) of the inorganic particles in the ultraviolet-shielding agent is preferably in a range of 1:9 to 5:5, and more preferably in a range of 2:8 to 4:6.

When Mv:Mm is set in a range of 1:9 to 5:5, the absorption effect of the organic ultraviolet absorbent and the scattering and reflection effect of the inorganic particles are efficiently exerted, and the synergic effect of the ultraviolet-shielding effect becomes easily obtainable.

The ultraviolet-shielding agent may have surfaces that are treated using 1% by mass to 20% by mass of organosiloxane with respect to the total amount of the ultraviolet-shielding agent as necessary.

When the surfaces of the ultraviolet-shielding agent are treated using organosiloxane, in a case in which, for example, zinc oxide is used as the inorganic particles, it is possible to suppress the elution of the zinc oxide to the outside.

Examples of the organosiloxane include dialkylalkoxysilane compounds, and, among the compounds, organopolysiloxane or denatured organopolysiloxane obtained by denaturing organopolysiloxane using one or two or more selected from the group consisting of alkyl groups, isocyanate groups, epoxy groups, acryl groups and alkyl silicon compounds are preferably used, and dimethylpolysiloxane (silicone oil) and denatured dimethylpolysiloxane (denatured silicone oil) obtained by denaturing dimethylpolysiloxane (silicone oil) are particularly preferable.

Next, each of the ultraviolet absorbent-containing resin and the inorganic particle-containing resin which configure the ultraviolet-shielding agent will be described in detail.

"Ultraviolet Absorbent-Containing Resin"

The ultraviolet absorbent-containing resin contains an organic ultraviolet absorbent. In a case in which the core portion is made of an organic ultraviolet absorbent-containing resin, the average particle diameter in the core portion is preferably 0.05 μm to 5 μm.

Here, when the average particle diameter in the core portion is less than 0.05 μm, the core portion easily aggregates with another core portion, and it becomes impossible to sufficiently develop an ultraviolet-shielding function, which is not preferable. On the other hand, when the average particle diameter in the core portion exceeds 5 μm, in a case in which the ultraviolet-shielding agent is used as a cosmetic preparation, the ultraviolet-shielding agent does not smoothly spread on skin, and, consequently, a rough feeling and the like are caused so as to deteriorate the touch feeling and the like, which means that the feeling of use of the ultraviolet-shielding agent becomes unsatisfactory, which is not preferable.

The content rate of the organic ultraviolet absorbent in the ultraviolet absorbent-containing resin is preferably 0.1% by mass to 80% by mass, more preferably 0.5% by mass to 50% by mass, and still more preferably 1% by mass to 30% by mass.

Here, when the content rate of the organic ultraviolet absorbent in the resin is less than 0.1% by mass, the amount of the organic ultraviolet absorbent is too small, and it becomes impossible to sufficiently develop the ultraviolet-shielding function of the organic ultraviolet absorbent. As a result, when it is necessary to sufficiently develop the ultraviolet-shielding function, a large amount of the resin is required such that material design becomes extremely difficult when manufacturing cosmetic preparations, which is not preferable. On the other hand, when the content rate exceeds 80% by mass, since the amount of the organic ultraviolet absorbent becomes relatively large with respect to the resin, consequently, the dispersibility of the organic ultraviolet absorbent in the resin degrades, and the homogeneity of the composition is impaired, which is not preferable.

<Resin>

The resin, which is a component of the ultraviolet absorbent-containing resin, is not particularly limited as long as a monomer can dissolve the organic ultraviolet absorbent, a polymer of the monomer has a high transparency, and the resin can be used as a raw material for cosmetic preparations.

As the resin monomer, only one monomer selected from the group including monomers of (meth)acrylic resins, acrylic acid esters, methacrylic acid esters, acrylic-styrene copolymers, acrylic-amide copolymers, acrylic-epoxy copolymers, acrylic-urethane copolymers, acrylic-polyester copolymers, silicon-acrylic copolymers, vinyl acetate resins, polyamide resins, epoxy resins, urethane resins, polyester resins, silicone resins and the like can be solely used, or a mixture of two or more can be used.

Among the above, a monomer of a (meth)acrylic resin is preferable due to the excellent transparency.

Examples of the monomers of (meth)acrylic resins include methyl acrylate, ethyl acrylate, propyl acrylate, n-butyl acrylate, isobutyl acrylate, hexyl acrylate, 2-ethyl hexyl acrylate, n-octyl acrylate, dodecyl acrylate, lauryl acrylate, stearyl acrylate, 2-chloroethyl acrylate, phenyl acrylate, methyl α-chloroacrylate, trifluoroethyl acrylate, tetrafluoropropyl acrylate, methyl methacrylate, ethyl methacrylate, propyl methacrylate, n-butyl methacrylate, isobutyl methacrylate, hexyl methacrylate, 2-ethyl hexyl methacrylate, n-octyl methacrylate, dodecyl methacrylate, lauryl methacrylate, stearyl methacrylate and the like.

In addition, examples of resin monomers that can be polymerized in combination with the monomer of the (meth)acrylic resin include styrene, o-methylstyrene, m-methylstyrene, p-methylstyrene, α-methylstyrene, o-ethylstyrene, m-ethylstyrene, p-ethylstyrene, 2,4-dimethylstyrene, p-n-butylstyrene, p-t-butylstyrene, p-n-hexylstyrene, p-n-octylstyrene, p-n-nonylstyrene, p-n-decylstyrene, p-n-dodecylstyrene, p-methoxystyrene, p-phenylstyrene, p-chlorostyrene, 3,4-dichlorostyrene, vinyl acetate, vinyl propionate, vinyl benzoate, vinyl butyrate, N-vinyl pyrovinyl, vinylidene fluoride, tetrafluoroethylene, hexafluoropropylene, butadiene, isoprene and the like.

Only one resin monomer may be solely polymerized and used, or a polymer of a combination of two or more resin monomers may be used. For example, in a case in which the monomer of a (meth)acrylic resin and a monomer of another resin are combined, the content rate of the monomer of a (meth)acrylic resin in the resin monomer is preferably 10% by mass or more, and more preferably 30% by mass or more from the viewpoint of transparency.

<Organic Ultraviolet Absorbent>

The organic ultraviolet absorbent is not particularly limited as long as the organic ultraviolet absorbent can be dissolved in the resin monomer, and examples thereof include dibenzoylmethane-based compounds, benzophenone derivatives, para-amino benzoic acid derivatives, methoxy cinnamic acid derivatives, salicylic acid derivatives and the like. Only one organic ultraviolet absorbent may be solely used, or a combination of two or more may be used.

In a case in which a dibenzoylmethane-based compound is used as the organic ultraviolet absorbent, a core shell structure obtained by forming a core portion using a metallic oxide-containing resin, and partially or fully coating the core portion with a dibenzoylmethane-based compound-containing resin.

It is known that, generally, the efficiency of ultraviolet absorption per unit dibenzoylmethane-based compound improves as the content rate of the dibenzoylmethane-based compound increases. Therefore, when the core portion is coated using the dibenzoylmethane-based compound, a high concentration of the dibenzoylmethane-based compound is locally present on surface portions of the metallic oxide-containing resin which is the core portion. That is, when the core shell structure is formed, the ultraviolet absorption efficiency per unit dibenzoylmethane-based compound increases, and an ultraviolet-shielding property improves.

"Inorganic Particle-Containing Resin"

The inorganic particle-containing resin contains inorganic particles. In a case in which the core portion is made of an inorganic particle-containing resin, the average particle diameter in the core portion is 0.05 µm to 5 µm, preferably 0.05 µm to 4.8 µm, and more preferably 0.05 µm to 1 µm.

Here, when the average particle diameter in the core portion is less than 0.05 µm, the core portion easily aggregates with another core portion, and it becomes impossible to sufficiently develop a function of scattering and reflecting ultraviolet rays, which is not preferable. On the other hand, when the average particle diameter in the core portion exceeds 5 µm, in a case in which the ultraviolet-shielding agent is used as a cosmetic preparation, the ultraviolet-shielding agent does not smoothly spread on skin, and, consequently, a rough feeling and the like are caused so as to deteriorate the touch feeling and the like, which means that the feeling of use of the ultraviolet-shielding agent becomes unsatisfactory, which is not preferable.

<Inorganic Particles>

The inorganic particles are not particularly limited as long as the inorganic particles can scatter and reflect ultraviolet rays, and metal particles, non-metal particles, metallic oxide particles, non-metallic oxide particles, mixtures or alloys thereof, and the like can be used. Examples of the inorganic particles include particles of zinc, titanium, cerium, iron, zirconium, tin, silicon, aluminum, cadmium, calcium, potassium, gold, silver, platinum, carbon, tungsten, copper, antimony, barium, magnesium, manganese, strontium, nickel, yttrium, europium, lanthanum and the like, particles of oxides of the above elements, and the like.

Among the above inorganic particles, inorganic particles having a refractive index of 1.9 or more are preferable since the light scattering and reflection effect is favorable. Examples of such inorganic particles include particles of zinc, titanium, cerium, iron, zirconium, tin, copper and the like, and particles of oxides of the above elements. The value of the refractive index is preferably higher; however, practically, the upper limit is approximately 6.

Furthermore, metallic oxide particles having an ultraviolet-shielding function are preferably used since ultraviolet rays of 380 nm to 400 nm can be further shielded. As a metallic oxide having an ultraviolet-shielding function, particles which include one or two or more selected from the group of zinc oxide, titanium oxide, cerium oxide and iron oxide and have an ultraviolet-shielding function can be used.

The average primary particle diameter of the inorganic particles is 0.003 µm to 0.1 µm, more preferably 0.01 µm to 0.05 µm, and still more preferably 0.02 µm to 0.04 µm.

Here, when the average primary particle diameter of the inorganic particles is less than 0.003 µm, the particle diameter is too small, and the light scattering and reflection effect degrades, which is not preferable. On the other hand, when the average primary particle diameter exceeds 0.1 µm, since the scattering coefficient of the particles with respect to visible light rays increases, the transparency significantly degrades, consequently, the optical transparency with respect to visible light rays degrades, and the transparency deteriorates, which is not preferable.

The inorganic particles being used may have surfaces treated using one or two or more selected from the group of silica, alumina and organopolysiloxane. In a case in which the surfaces of the inorganic particles are treated using one or two or more selected from the group of silica, alumina and organopolysiloxane, since the surfaces are covered, for example, metallic ions that configure the metallic oxide do not easily flow outside, and the surface activity of the metallic oxide is further suppressed, which is preferable.

The content rate of the inorganic particles in the inorganic particle-containing resin is preferably 1% by mass to 80% by mass, more preferably 5% by mass to 70% by mass, and still more preferably 10% by mass to 60% by mass.

Here, when the content rate of the inorganic particles in the resin is less than 1% by mass, the amount of the inorganic particles is too small, and it becomes impossible to sufficiently develop the ultraviolet scattering and reflection function of the inorganic particles, which is not preferable. On the other hand, when the content rate exceeds 80% by mass, since the amount of the inorganic particles becomes relatively large with respect to the resin, consequently, the dispersibility of the inorganic particles in the resin degrades, and the homogeneity of the composition is impaired, which is not preferable.

<Resin>

The resin, which is a component of the inorganic particle-containing resin, is not particularly limited as long as a polymer of a monomer has a high transparency, and the resin can be used as a raw material of cosmetic preparations.

Since exactly the same monomer as the resin described in the above "resin" can be used as the resin, the resin will not be described.

In the ultraviolet-shielding agent, it is preferable to use a combination of the inorganic particle-containing resin and the ultraviolet absorbent-containing resin which are appropriately combined in consideration of wavelength ranges in which the inorganic particles included in the inorganic particle-containing resin and the organic ultraviolet absorbent included in the ultraviolet absorbent-containing resin can absorb and shield ultraviolet rays.

For example, zinc oxide is an n-type metallic oxide semiconductor, and the band gap energy in the band structure is 3.2 eV. Therefore, when light having energy larger than the band gap energy is radiated on the zinc oxide, electrons absorb light energy and are excited from the valence band to the conduction band. Since the absorption edge of the zinc oxide is near 380 nm, zinc oxide can absorb ultraviolet rays in a wavelength range from long wavelength ultraviolet rays (UVA) to middle wavelength ultraviolet rays (UVB).

Therefore, in a case in which zinc oxide particles are used, an organic ultraviolet absorbent that can shield long wavelength ultraviolet rays (UVA) or an organic ultraviolet absorbent that can shield middle wavelength ultraviolet rays (UVB) is preferably combined.

In addition, while titanium oxide has a band gap energy at 3.0 eV to 3.2 eV in the band structure, since electron excitation in titanium oxide is indirect transition, titanium oxide begins to absorb light from near 320 nm which is a far lower wavelength than an absorption wavelength estimated from the value of the energy gap.

Therefore, in a case in which titanium oxide particles are used, an organic ultraviolet absorbent that can shield long wavelength ultraviolet rays (UVA) is preferably combined.

Specific examples of the combination include a combination of any one of zinc oxide which can shield ultraviolet rays in a wavelength range of 380 nm or less and titanium oxide which can shield ultraviolet rays in a wavelength range of 320 nm or less and avobenzone having an absorption maximum of 358 nm to 360 nm.

In a case in which the resin is made to contain any one of zinc oxide and titanium oxide, and avobenzone so as to produce a core shell structure, an effect of developing the ultraviolet-shielding function from a longer wavelength than in a case in which resin particles solely including each of zinc oxide, titanium oxide and avobenzone are used can be obtained. That is, a synergic effect of the ultraviolet-shielding effect can be obtained.

The reasons for the enhancement of the ultraviolet-shielding effect of the resin particles formed by coating the core portion made of any one resin of the organic ultraviolet absorbent-containing resin and the inorganic particle-containing resin with the coating layer made of the other resin or both resins are considered as follows.

In a case in which light transmits through the ultraviolet-shielding agent of the embodiment, first, ultraviolet rays are absorbed or scattered and reflected by the resin that coats the core portion, then, scattered, reflected or absorbed by the resin in the core portion, and, again, absorbed or scattered and reflected by the resin that coats the core portion.

In addition, since the ultraviolet rays transmit through the ultraviolet-shielding agent due to the inorganic particles while being repeatedly scattered and reflected, there is a higher opportunity for ultraviolet rays to be absorbed by the organic ultraviolet absorbent compared with a case in which ultraviolet rays transmit through an ultraviolet-shielding agent not including the inorganic particle-containing resin.

That is, it is considered that, since ultraviolet rays are shielded due to both the light absorption effect of the organic ultraviolet absorbent and the ultraviolet scattering and reflection effect of the inorganic particles, the ultraviolet-shielding effect is favorable compared with a case in which either the organic ultraviolet absorbent or the inorganic particles are solely used, and, particularly, a synergic effect with which ultraviolet rays in a wavelength range of 380 nm to 400 nm can be shielded can be obtained.

In addition, since light transmits through the ultraviolet-shielding agent while being repeatedly scattered and reflected by the inorganic particles, light passes through the ultraviolet absorbent-containing resin and the inorganic particle-containing resin in the ultraviolet-shielding agent many times while being repeatedly scattered and reflected by the inorganic particles. As a result, ultraviolet rays are further shielded, and therefore it is considered that ultraviolet rays near 380 nm to 400 nm can be shielded, which could not be achieved in the past.

[Method for Producing Ultraviolet-Shielding Agents]

A method for producing ultraviolet-shielding agents of the embodiment is configured of a step of obtaining a resin monomer-dispersed liquid by dispersing inorganic particles in a resin monomer including a dispersant, a step of obtaining a resin monomer-dissolved liquid by dissolving an organic ultraviolet absorbent and a dispersant in the resin monomer, a step of obtaining a dispersion liquid containing a core portion made of an organic ultraviolet absorbent-containing resin or an inorganic particle-containing resin (hereinafter, may be referred to as "core resin particle dispersion liquid") by suspending or emulsifying the resin monomer-dispersed liquid or the resin monomer-dissolved liquid in pure water including a suspension protectant, a silicone-based defoamer and a crosslinking agent, and then adding a polymerization initiator so as to carry out suspension polymerization or emulsification polymerization, thereby, a step of obtaining a coating resin by suspending or emulsifying the resin monomer-dispersed liquid or the resin monomer-dissolved liquid in pure water containing a polymerization initiator, and a step of obtaining an ultraviolet-shielding agent including resin particles having a core shell structure by mixing the coating resin and the dispersion liquid containing the core portion so as to carry out suspension polymerization or emulsification polymerization.

A method for producing ultraviolet-shielding agents having the core shell structure will be described in detail.

Here, for the convenience of description, a case in which a resin containing inorganic particles is used as the core portion, and the core portion is coated with a resin containing an organic ultraviolet absorbent will be described.

Meanwhile, in a case in which the core portion is formed of a resin containing the organic ultraviolet absorbent and coated with a resin containing the inorganic particles, the method may be similarly carried out with the positions of the monomer-dispersed liquid and the monomer-dissolved liquid exchanged with each other.

(1) Manufacturing of the Resin Monomer-Dispersed Liquid

First, inorganic particles are dispersed in a resin monomer including a dispersant, thereby producing a resin monomer-dispersed liquid.

Since the inorganic particles having an ultraviolet-shielding function are exactly the same as the inorganic particles described in the <inorganic particles>, the inorganic particles will not be described.

In a case in which the inorganic particles are dispersed in the resin monomer, the average dispersed particle diameter is preferably 0.003 μm to 0.1 μm.

Here, when the average dispersed particle diameter of the inorganic particles in the resin monomer exceeds 0.1 μm, since the scattering coefficient of the resin particles with respect to visible light rays increases, the transparency significantly degrades. As a result, the transparency degrades, and there is a concern that the resin monomer may be devitrified depending on cases, which is not preferable.

The dispersant preferably has a high affinity to the resin monomer, and is preferably highly hydrophobic. That is, the dispersant coats the inorganic particles so as to accelerate dispersion in the resin monomer, simultaneously, most of the inorganic particles turn into a mono-dispersion state within a relatively short period of time, and the average dispersed particle diameter becomes 0.003 μm to 0.1 μm.

In addition, since the dispersant makes the inorganic particles hydrophobic, the dispersant assists the inorganic particles to be incorporated into the resin while preventing the inorganic particles from escaping outside the polymer and transiting into a water phase.

Examples of the dispersant include carboxylic acids or salts thereof such as sodium carboxymethyl cellulose, sulfonic acids or salts thereof such as sodium alkane sulfonate, sulfate esters or salts thereof such as sodium polyoxyethylene nonyl phenyl ether sulfate, phosphate esters or salts thereof such as polyoxy ethylene alkyl phenyl ether phosphate or polyoxy ethylene alkyl ether phosphate, and phosphonic acids or salts thereof such as sodium lauryl phosphate. Only one dispersant may be solely used, or a mixture of two or more may be used.

Particularly, in a case in which the ultraviolet-shielding agent of the embodiment is used in cosmetic preparations, the dispersant is supposed to be recognized as a raw material of cosmetic preparations at the same time.

The addition rate of the dispersant to the inorganic particles is preferably 1% by mass to 50% by mass. When the addition rate is less than 1% by mass, the amount is too small to cover the surfaces of the inorganic particles such that sufficient inorganic particles in a dispersion state cannot be obtained. On the other hand, when the addition rate exceeds 50% by mass, the dispersibility does not further improve even at a higher addition rate, and the dispersant is wasted.

A dispersion apparatus being used is not particularly limited as long as the apparatus supplies a sufficient amount of dispersion energy to a dispersion system, and examples thereof include ball mills, sand mills, ultrasonic dispersion apparatuses, homogenizers and the like.

The dispersion period is preferably approximately 30 minutes to 3 hours, and an appropriate period may be selected depending on a combination of the status of the dispersion state and the production costs.

Based on what has been described above, a resin monomer-dispersed liquid having an average dispersed particle diameter of the inorganic particles of 0.003 μm to 0.1 μm can be obtained.

(2) Production of the Resin Monomer-Dissolved Liquid

First, an organic ultraviolet absorbent is dissolved in a resin monomer, thereby producing a resin monomer-dissolved liquid.

Since the organic ultraviolet absorbent is exactly the same as the organic ultraviolet absorbent described in the <organic ultraviolet absorbent>, the organic ultraviolet absorbent will not be described.

Next, 1% by mass to 50% by mass of the dispersant is mixed with the resin monomer-dissolved liquid. Since the dispersant is exactly the same as the dispersant described when producing the resin monomer-dispersed liquid, the dispersant will not be described.

The addition rate of the dispersant is preferably 1% by mass to 50% by mass with respect to the resin monomer-dissolved liquid. The reasons for what has been described above are as follows. When the addition rate is less than 1% by mass, the emulsion coating strength of a suspended liquid or an emulsified liquid, which will be described below, does not increase, and consequently, the polymerization efficiency of suspension polymerization or emulsification polymerization decreases. On the other hand, when the addition rate exceeds 50% by mass, the polymerization efficiency cannot be further improved even at a higher addition rate, and the dispersant is wasted.

Based on what has been described above, a resin monomer-dissolved liquid containing the organic ultraviolet absorbent can be obtained.

(3) Manufacturing of the Dispersion Liquid Including the Core Portion

First, the resin monomer-dispersed liquid is suspended or emulsified in pure water including a suspension protectant, a silicone-based defoamer and a crosslinking agent, thereby producing a suspended liquid or an emulsified liquid having a dispersed particle diameter of 0.05 μm to 5 μm.

Examples of the suspension protectant include nonionic surfactants such as polyoxyethylene alkyl ether and polyoxyethylene alkyl phenyl ether, anionic surfactants such as alkyl benzene sulfonate, alkyl sulfate ester salts and alkyl phenyl sulfate ester salts, and the like, and, among the above, the anionic surfactants are preferable, and the anionic surfactant is preferably alkyl benzene sulfonate.

The addition amount of the suspension protectant is 0.1% by mass to 10% by mass, and more preferably 0.1% by mass to 2% by mass with respect to the resin monomer-dispersed liquid.

Examples of the silicone-based defoamer include oil-type defoamers, oil compound-type defoamers, solution-type defoamers, powder-type defoamers, solid-type defoamers, emulsion-type defoamers, self-emulsification-type defoamers and the like, and, among the above, the oil compound-type defoamers are preferable.

The addition amount of the silicone-based defoamer is preferably 0.01% by mass to 5% by mass, and more preferably 0.1% by mass to 1% by mass with respect to the resin monomer-dispersed liquid.

When 0.01% by mass to 5% by mass of the silicone-based defoamer is added to the resin monomer-dispersed liquid, the stirring velocity of mixers, stirrers, homo mixers, homogenizers and the like can be significantly increased, and the core portion can be miniaturized to approximately 50 nm. Therefore, the stirring velocity of mixers, stirrers, homo mixers, homogenizers and the like can be significantly increased. As a result, the production efficiency of the core portion can be improved, and the production costs can be significantly reduced.

The crosslinking agent is not particularly limited as long as the crosslinking agent is a monomer having two or more unsaturated double bonds, and can be appropriately selected from polyfunctional vinyl monomers, polyfunctional (meth) acrylate ester acid derivatives and the like.

More specific examples thereof include (poly)alkylene glycol-based di(meth)acrylates such as divinyl benzene, divinyl biphenyl, divinyl naphthalene, (poly)ethylene glycol di(meth)acrylate, (poly) propylene glycol di(meth)acrylate and (poly)tetramethylene glycol di(meth)acrylate.

In addition, examples thereof include alkanediol-based (meth)acrylates such as 1,6-hexanediol di(meth)acrylate, 1,8-octanediol di(meth)acrylate, 1,9-nonanediol di(meth) acrylate, 1,10-decanediol di(meth)acrylate, 1,12-dodecanediol di(meth)acrylate, 3-methyl-1,5-pentanediol di(meth)acrylate, 2,4-diethyl-1,5-pentanediol di(meth)acrylate, butyl ethyl propanediol di(meth)acrylate, 3-methyl-1,7-octanediol di(meth)acrylate and 2-methyl-1,8-octanediol di(meth)acrylate.

In addition, examples thereof include neopentyl glycol di(meth)acrylate, trimethylol propane tri(meth)acrylate, tetramethylol methane tri(meth)acrylate, tetramethylol propane tetra(meth)acrylate, pentaerythritol tri(meth)acrylate, ethoxylated cyclohexane dimethanol di(meth)acrylate, ethoxylated bisphenol A di(meth)acrylate, tricyclodecane dimethanol di(meth)acrylate, propoxylated ethoxylated bisphenol A di(meth)acrylate, 1,1,1-trishydroxy methylethane di(meth)acrylate, 1,1,1-trishydroxy methylethane tri (meth)acrylate, 1,1,1-trishydroxy methyl propane triacrylate, diacryl phthalate and isomers thereof, triaryl isocyanurate and derivatives thereof, and the like.

Among the above, (poly)ethylene glycol di(meth)acrylate is particularly preferable.

The addition amount of the crosslinking agent is preferably 0.1% by mass to 10% by mass, and more preferably 1% by mass to 10% by mass with respect to the resin monomer-dispersed liquid.

The pure water is not particularly limited as long as the pure water is water ordinarily used for cosmetic preparations, and examples thereof include ion exchange water, distilled water, purified water, ultrapure water, natural water, alkali ion water, deep water and the like.

Next, a polymerization initiator is added to the suspended liquid or the emulsified liquid, and suspension polymerization or emulsification polymerization is carried out.

Examples of the polymerization initiator include persulfates such as potassium persulfate and ammonium persulfate; organic peroxides such as hydrogen peroxide, benzoyl peroxide, lauroyl peroxide, t-butyl hydroperoxide, benzoyl peroxide and cumene hydroperoxide; azo-based initiators such as azobis diisobutylonitrile, 2,2-azobis(2-amidinopropane) dihydrochloride; and the like, and, among the above, persulfates are preferable.

The addition amount of the polymerization initiator is preferably 0.01% by mass to 1% by mass, and more preferably 0.05% by mass to 0.5% by mass with respect to the resin monomer-dispersed liquid which serves as a starting material.

The polymerization method is preferably a method in which the suspended liquid or the emulsified liquid is heated under stirring in a nitrogen atmosphere or in the presence of the polymerization initiator, thereby initiating polymerization.

The polymerization initiating temperature is preferably 50° C. to 80° C. The period during which the suspended liquid or the emulsified liquid is polymerized while maintaining the temperature is preferably approximately 1 hour to 5 hours, and an appropriate period may be selected depending on a period during which the amount of unreacted residual monomers is minimized and a combination of the polymerization state and the production costs.

After that, the suspended liquid or the emulsified liquid is cooled using ice or naturally cooled, and the polymerization reaction is stopped, whereby a dispersion liquid including the core portion made of an inorganic particle-containing resin can be obtained.

In the suspension polymerization or emulsification polymerization, the content rates of the suspension protectant, the silicone-based defoamer and the polymerization initiator are limited in the above ranges, the average particle diameter of the obtained core portion can be controlled to 0.05 µm to 5 µm.

(4) Suspension and Emulsification of the Coating Resin

The resin monomer-dissolved liquid is suspended or emulsified in pure water including 0.01% by mass to 1% by mass of the polymerization initiator with respect to the resin monomer-dissolved liquid, thereby producing a suspended liquid or an emulsified liquid of the coating resin.

Since the polymerization initiator and the pure water are exactly the same as the polymerization initiator and the pure water described in the "polymerization initiator" and the "pure water", the polymerization initiator and the pure water will not be described.

(5) Manufacturing of the Core Shell Structure

The suspended liquid or the emulsified liquid of the coating resin and the dispersion liquid including the core portion are mixed, then, polymerized, washed, dried and cracked, whereby an ultraviolet-shielding agent having the core shell structure can be obtained.

The resin monomer-dissolved liquid and the dispersion liquid including the core portion are preferably mixed at a mixing ratio in which the mass ratio between the organic ultraviolet absorbent and the inorganic particles is in a range of 1:9 to 5:5.

When the resin monomer-dissolved liquid and the dispersion liquid including the core portion are mixed in the above range, a synergic effect of the ultraviolet-shielding functions of the organic ultraviolet absorbent and the inorganic particles can be obtained.

Since the polymerization method is exactly the same as the polymerization method of the suspended liquid or the emulsified liquid, the polymerization method will not be described.

Next, the obtained polymerized substance is washed using pure water. In this washing step, in order to further improve the washing efficiency, the polymerized substance may be washed using an alcohol or the like before washed using pure water. Thereby, monomers remaining in the polymerized substance, the polymerization initiator and the surfactant are removed.

Any alcohol may be used as the alcohol as long as the alcohol is soluble in pure water, and can be easily washed away, examples thereof include ethanol, 2-propanol and the like, and 2-propanol is particularly preferable.

The washing method is not particularly limited as long as the residual monomers and the like can be removed, and pressure filtration, suction filtration, filter pressing, centrifugal separation, ultrafiltration, decantation and the like are preferable.

After the end of the washing, the obtained polymerized substance is dried at 80° C. to 100° C., and pure water and the like remaining in the polymerized substance are removed. The drying method is not particularly limited as long as the alcohol or pure water can be removed, and examples thereof include drying in the atmospheric pressure, vacuum drying and the like.

Next, the dried polymerized substance is cracked. The cracking method is not particularly limited as long as the respective particles can be cracked, and examples thereof include pin milling, hammer milling, jet milling, impeller milling and the like.

Thereby, an ultraviolet-shielding agent having the core shell structure can be generated.

When the ultraviolet-shielding agent is made to pass through a cracking step, the respective particles aggregated due to drying are cracked, and the feeling in use can be improved when the ultraviolet-shielding agent is used for cosmetic preparations.

[Ultraviolet-Shielding Agent-Containing Dispersion Liquid]

The ultraviolet-shielding agent-containing dispersion liquid of the embodiment is a dispersion liquid obtained by dispersing the ultraviolet-shielding agent in a dispersion medium, and the content rate of the ultraviolet-shielding agent is 1% by mass to 80% by mass, more preferably 20% by mass to 70% by mass, and still more preferably 30% by mass to 60% by mass.

Any solvent may be used as the dispersion medium as long as the solvent can disperse the ultraviolet-shielding agent, and examples thereof that are preferably used include water; alcohols such as methanol, ethanol, 2-propanol, butanol and octanol; esters such as ethyl acetate, butyl acetate, ethyl lactate, propylene glycol monomethyl ether acetate, propylene glycol monoethyl ether acetate and γ-butyrolactone; ethers such as diethyl ether, ethylene glycol monomethyl ether (methyl cellosolve), ethylene glycol monoethyl ether (ethyl cellosolve), ethylene glycol monobutyl ether (butyl cellosolve), diethylene glycol monomethyl ether and diethylene glycol monoethyl ether; ketones such as acetone, methyl ethyl ketone, methyl isobutyl ketone, acetyl acetone and cyclohexanone; aromatic hydrocarbons such as benzene, toluene, xylene and ethylbenzene; amides such as dimethyl formamide, N,N-dimethylacetamide and N-methylpyrrolidone; chain-like polysiloxanes such as dimethyl polysiloxane, methyl phenyl polysiloxane and diphenyl polysiloxane; cyclic polysiloxanes such as octamethyl cyclotetrasiloxane, decamethyl cyclopentasiloxane and dodecamethyl cyclohexanesiloxane; and denatured polysiloxanes such as amino-denatured polysiloxane, polyether-denatured polysiloxane, alkyl-denatured polysiloxane and fluorine-denatured polysiloxane, and, among the above solvents, only one solvent or a mixture of two or more solvents can be used.

Here, when the content rate of the ultraviolet-shielding agent is less than 1% by mass, the amounts of the organic ultraviolet absorbent and the metallic oxide particles are too small, the dispersion liquid cannot sufficiently develop the ultraviolet-shielding function, and, consequently, material design becomes extremely difficult when manufacturing cosmetic preparations, which is not preferable. On the other hand, when the content rate exceeds 80% by mass, the amount of the ultraviolet-shielding agent in the dispersion liquid becomes relatively large, consequently, the dispersibility of the ultraviolet-shielding agent in the dispersion liquid degrades, and the homogeneity of the composition is impaired, which is not preferable.

The dispersion liquid can be obtained by mixing the ultraviolet-shielding agent with the dispersion medium, mixing a dispersant or a water-soluble binder with the mixture as necessary, subsequently, carrying out a dispersion treatment on the mixture using a disperser or a mixer such as a bead mill, a ball mill or a homogenizer in which sand mills or zirconia beads are used, and dispersing the ultraviolet-shielding agent in the dispersion medium.

In addition, the period necessary for the dispersion treatment is not particularly limited as long as the period is a sufficient time for the ultraviolet-shielding agent to be dispersed in the dispersion medium.

Here, as specific examples of the ultraviolet-shielding agent-containing dispersion liquid, an ultraviolet-shielding agent-containing silicone dispersion liquid including the ultraviolet-shielding agent dispersed in silicone and an ultraviolet-shielding agent-containing aqueous dispersion liquid including the ultraviolet-shielding agent dispersed in water will be described.

[Ultraviolet-Shielding Agent-Containing Silicone Dispersion Liquid]

The ultraviolet-shielding agent-containing silicone dispersion liquid of the embodiment is an ultraviolet-shielding agent-containing silicone dispersion liquid formed by dispersing the ultraviolet-shielding agent in silicone, in which the content rate of the ultraviolet-shielding agent is 1% by mass to 80% by mass, more preferably 20% by mass to 70% by mass, and still more preferably 30% by mass to 60% by mass.

The silicone may be a cyclic silicone having a structure skeleton represented by the formula (1) or a linear silicone, and is not particularly limited.

Examples of the silicone include dimethylpolysiloxane, methyl phenyl polysiloxane, hexamethylcyclotrisiloxane, octamethylcyclotetrasiloxane, decamethylpentasiloxane and methyl trimethicone.

[Chem. 1]

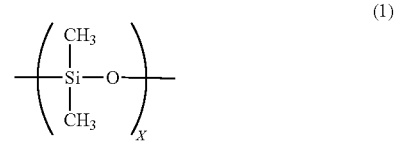

(1)

In the formula (1), X is preferably in a range of 1 to 2000. When X is set in the above range, the mixing with the ultraviolet-shielding agent of the embodiment becomes easy, which is preferable.

The dispersant is not particularly limited as long as the dispersant can disperse the ultraviolet-shielding agent in silicone, and examples thereof include polyether-denatured silicone, polyglycerine-denatured silicone, amino-denatured silicone, phenyl-denatured silicone, alkyl-denatured silicone, carbonyl-denatured silicone, dimethyl silicone and the like. The content rate of the dispersant is preferably in a range of 1% by mass to 50% by mass with respect to the total mass of the ultraviolet-shielding agent.

In addition, a natural oil, a moisturizing agent, a viscosity improver, a perfume, a preservative and the like may be further mixed with the dispersion liquid obtained by dispersing the silicone and the dispersant using a sand mill, a homogenizer or the like.

When the content rate of the dispersant is adjusted in the above range, transparency can be sufficiently ensured in a case in which the ultraviolet-shielding agent-containing silicone dispersion liquid is spread and coated on skin even when the ultraviolet-shielding agent-containing silicone dispersion liquid is solely used, or directly mixed with cosmetic preparations.

[Ultraviolet-Shielding Agent-Containing Aqueous Dispersion Liquid]

The ultraviolet-shielding agent-containing aqueous dispersion liquid of the embodiment is an ultraviolet-shielding agent-containing aqueous dispersion liquid which is formed by dispersing the ultraviolet-shielding agent in an aqueous dispersion medium including an alcohol, and contains the ultraviolet-shielding agent at a content rate of 1% by mass to 80% by mass, more preferably 20% by mass to 70% by mass, and still more preferably 30% by mass to 60% by mass, and 5% by mass to 20% by mass of the alcohol.

The aqueous dispersion liquid may further contain water-soluble macromolecules in 0.001% by mass to 10% by mass, more preferably 0.005% by mass to 5% by mass, and still more preferably 0.01% by mass to 3% by mass. In this case, it is necessary to adjust the content rates of the respective components so that the total content rate of the respective components of the ultraviolet-shielding agent, the alcohol and the water-soluble macromolecules does not exceed 100% by mass.

Examples of the alcohol include monovalent alcohols having 1 to 6 carbon atoms, such as ethanol, 1-propanol, 2-propanol, 1-butanol, 2-butanol, glycerin, 1,3-butylene glycol, propylene glycol and sorbitol, and multivalent alcohols and, among the above, a monovalent alcohol, particularly, ethanol is preferable.

In a case in which the aqueous dispersion liquid does not include the water-soluble macromolecules, the content rate of the alcohol is preferably 5% by mass to 20% by mass, and more preferably 10% by mass to 20% by mass.

Particularly, in a case in which the content rate of the alcohol is set in a range of 10% by mass to 20% by mass, the dispersibility and aging stability of the ultraviolet-shielding agent in the aqueous dispersion liquid can be improved, which is preferable.

In addition, in a case in which the aqueous dispersion liquid includes the water-soluble macromolecules, the water-soluble macromolecules are not particularly limited as long as the water-soluble macromolecules can be used for cosmetic preparations, and examples thereof include gum arabic, sodium alginate, casein, carrageenan, galactan, carboxyvinyl polymers, carboxymethyl cellulose, carboxymethylcellulose sodium, carboxymethyl starch, agar, xanthan gum, quince seed, guar gum, collagen, gelatin, cellulose, dextran, dextrin, tragacanth gum, hydroxyethyl cellulose, hydroxypropyl cellulose, hyaluronic acid sodium pectin, pullulan, methyl cellulose, methyl hydroxypropyl cellulose and the like. Only one kind of the water-soluble macromolecule may be solely used, or a mixture of two or more kinds may be used.

The water-soluble macromolecules play roles of a dispersant and a viscosity adjuster, and the addition of the water-soluble macromolecules also improves the dispersibility and aging stability of the ultraviolet-shielding agent in the aqueous dispersion liquid.

In a case in which the aqueous dispersion liquid includes the water-soluble macromolecules, the content rate of the alcohol is preferably 5% by mass to 20% by mass, and more preferably 15% by mass to 20% by mass.

Here, the reasons for setting the content rate of the alcohol in a case in which the aqueous dispersion liquid includes the water-soluble macromolecules to 5% by mass to 20% by mass are that, when the content rate is less than 5% by mass, since the content amount of the alcohol is too small, the water-soluble macromolecules cannot uniformly infiltrate into the alcohol and are unevenly swollen by moisture, consequently, the dispersibility of the ultraviolet-shielding agent degrades such that it becomes difficult to handle the ultraviolet-shielding agent, and, furthermore, the aging stability of the aqueous dispersion liquid degrades, which is not preferable. In addition, when the content rate exceeds 20% by mass, the viscosity of the entire aqueous dispersion liquid increases such that the dispersion stability of the ultraviolet-shielding agent degrades, and the aging stability of the aqueous dispersion liquid also degrades, which is not preferable.

The ultraviolet-shielding agent-containing aqueous dispersion liquid can be obtained by mixing the ultraviolet-shielding agent with a mixture (dispersion medium) which includes a solvent (dispersion medium) including the alcohol or the alcohol and the water-soluble macromolecules, then, adding water, and dispersing the ultraviolet-shielding agent. The amount of the water needs to be appropriately adjusted, and is preferably in a range of 15% by mass to 94% by mass.

When the amount of the water is adjusted in the above range, it is possible to obtain the ultraviolet-shielding agent-containing aqueous dispersion liquid that can sufficiently ensure transparency in a case in which the ultraviolet-shielding agent-containing aqueous dispersion liquid is spread and coated on skin even when the ultraviolet-shielding agent-containing aqueous dispersion liquid is solely used, or mixed with cosmetic preparations.

[Cosmetic Preparation]

The cosmetic preparation of the embodiment is a cosmetic preparation containing any one or both of the ultraviolet-shielding agent and the ultraviolet-shielding agent-containing dispersion liquid in 1% by mass to 60% by mass in terms of the ultraviolet-shielding agent, and, when the cosmetic preparation contains the ultraviolet-shielding agent in the above range, there is no concern of white turbidity, transparency can be sufficiently ensured, furthermore, there is no rough feeling and the like, and the feeling in use becomes excellent.

The cosmetic preparation can be obtained by blending any one or both of the ultraviolet-shielding agent and the ultraviolet-shielding agent-containing dispersion liquid with emulsion, cream, foundation, lipsticks, rouge, eye shadow and the like as blended in the past.

Furthermore, when any one or both of the ultraviolet-shielding agent and the ultraviolet-shielding agent-containing dispersion liquid are blended with aqueous cosmetic preparations, such as cosmetic water and sunscreen gels, for which it was difficult to formulate the ultraviolet-shielding agent and the ultraviolet-shielding agent-containing dispersion liquid in the past, for example, in a case in which zinc oxide is used as the inorganic particles, the elution of zinc is suppressed, and aqueous cosmetic preparations that are excellent in terms of the ultraviolet-shielding function, transparency and the feeling in use can be obtained.

When the cosmetic preparation is used as a component of cosmetics, it is possible to provide a variety of cosmetics such as skin care cosmetics, makeup cosmetics and body care cosmetics which are excellent in terms of the ultraviolet-shielding function, transparency and the feeling in use. Particularly, the cosmetic preparation is preferable for whitening of skin care cosmetics, base makeup of makeup cosmetics and sunscreening of body care cosmetics which require the ultraviolet-shielding function.

As described above, since the ultraviolet-shielding agent of the embodiment includes the resin particles formed by coating the core portion made of any one resin of the organic ultraviolet absorbent-containing resin and the inorganic particle-containing resin with the coating layer made of the other resin or both resins, it is possible to enhance the effect of shielding ultraviolet rays, particularly, ultraviolet rays having a wavelength of 380 nm to 400 nm using the synergic effect of the ultraviolet absorption effect of the organic ultraviolet absorbent and the scattering and reflection effect of the inorganic particles. In addition, in a case in which metallic oxide particles are used as the inorganic particles, it is possible to prevent changes in the qualities or colors of cosmetic preparations and the degradation of the feeling in use which are caused by the organic ultraviolet absorbent recrystallized due to the influence of metallic ions included in the metallic oxide particles in the presence of ultraviolet rays, to enhance photostability, and to stabilize the qualities of cosmetic preparations.

In addition, since it is not necessary to dissolve the organic ultraviolet absorbent in a specific solvent, it is possible to blend the ultraviolet-shielding agent of the embodiment with not only water-in-oil (W/O) cosmetic preparations but also oil-in-water (O/W) cosmetic preparations, for which it was difficult to formulate the ultraviolet-shielding agent in the past, and aqueous cosmetic preparations, such as cosmetic water and sunscreen gels. Therefore, it is possible to improve the degree of freedom of the formulation of cosmetic preparations.

In addition, since the average particle diameter of the ultraviolet-shielding agent is set to 0.1 μm to 5 μm, even in a case in which the ultraviolet-shielding agent is used in cosmetics, there is no rough feeling, and the feeling in use is excellent.

In addition, since the inorganic particles having an average particle diameter of 0.003 μm to 0.1 μm are included in the resin, visible light rays are not absorbed, and transparency, which is considered to be important for cosmetic preparations, can be maintained.

In addition, in a case in which a (meth)acrylic resin is used as the resin, superior transparency can be maintained.

In addition, in a case in which the ultraviolet-shielding agent is manufactured by combining any one or both of zinc oxide and titanium oxide and the organic ultraviolet absorbent that can shield long-wavelength ultraviolet rays (UVA), it is possible to shield ultraviolet rays (UV) having a wavelength of 380 nm to 400 nm.

Furthermore, when the cosmetic preparation of the embodiment is used as a component of cosmetics, it is possible to provide a variety of cosmetics such as skin care cosmetics, makeup cosmetics and body care cosmetics which are excellent in terms of the ultraviolet-shielding function, transparency, the feeling in use and safety. Particularly, in a case in which the cosmetic preparation is used for whitening of skin care cosmetics, base makeup of makeup cosmetics and sunscreening of body care cosmetics which require the ultraviolet-shielding function, it is possible to provide cosmetics which are excellent in terms of the ultraviolet-shielding function, transparency, the feeling in use and safety.

Meanwhile, the ultraviolet-shielding agent of the embodiment and the dispersion liquid including the ultraviolet-shielding agent can also be used in weather-resistant paints and the like which require the ultraviolet-shielding function.

In addition, in a case in which the ultraviolet-shielding agent is used in non-cosmetic fields, there are many cases in which the rough feeling, the feeling in use and the like, which are considered to be important for cosmetics, do not significantly matter, dispersants or resins can be widely selected, and the degree of freedom for the design blending of paints and the like can be increased.

According to method for producing ultraviolet-shielding agents of the embodiment, it is possible to efficiently produce the ultraviolet-shielding agents of the embodiment using a simple apparatus, and to reduce production costs.

EXAMPLES

Hereinafter, the invention will be specifically described using Examples and Comparative Examples, but the invention is not limited to Examples.

Example 1

Manufacturing of Core Shell-Type Ultraviolet-Shielding Agent

A. Manufacturing of a Core Resin Particle-Dispersed Liquid Containing Fine Zinc Oxide Particles which Forms the Core Portion Fine zinc oxide particles having an average primary particle diameter of 0.02 μm (manufactured by Sumitomo Osaka Cement Company, Limited, 200 parts by mass), methyl methacrylate (188 parts by mass) and a phosphate ester-type surfactant (12 parts by mass) were mixed and dispersed using a sand mill for 2 hours, thereby obtaining a monomer (MMA)-dispersed liquid including fine zinc oxide particles dispersed in methyl methacrylate.

Next, the obtained monomer (MMA)-dispersed liquid (105.0 parts by mass), pure water (229.5 parts by mass), sodium dodecylbenzenesulfonate (0.5 parts by mass), ethylene glycol dimethacrylate (14.0 Parts by mass) and a silicone-based defoamer (1.0 parts by mass) were mixed and stirred using a homogenizer, thereby obtaining an emulsion.

Next, the obtained emulsion (320.0 parts by mass), pure water (79.856 parts by mass) and potassium persulfate (0.144 parts by mass) were mixed, moved to a reaction apparatus equipped with a stirrer and a thermometer, and substituted by nitrogen at room temperature for 1 hour. Next, the emulsion was heated and held at 65° C. for 3 hours so as to cause a polymerization reaction, and then cooled using ice so as to stop the polymerization reaction, thereby obtaining a core resin particle-dispersed liquid.

After that, some of the core resin particle-dispersed liquid was sampled, washed using pure water, and then dried at 90° C. After that, the obtained dried substance was cracked using a hammer mill, thereby obtaining core resin particles.

In addition, the core resin particles (60 parts by mass), decamethyl cyclopentasiloxane (D5) SH245 (manufactured by Dow Corning Toray Co., Ltd., 51 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core resin particle D5-dispersed liquid containing fine zinc oxide particles.

Next, the obtained core resin particle D5-dispersed liquid was diluted 5 times by adding D5 with masses of 4 times, the dispersed particle diameters of core resin particles in the diluted liquid were measured using a dynamic light scattering particle size distribution measurement apparatus LB-550 (manufactured by Horiba, Ltd.), and the volume particle size distribution and cumulative volume particle size distribution were computed. As a result, the particle diameter at the 10 volume % point (D10) in the cumulative volume particle size distribution was 163.6 nm, the particle diameter at the 50 volume % point (D50) was 221.9 nm, and the particle diameter at the 90 volume % point (D90) was 287.6 nm. The volume particle size distribution and cumulative volume particle size distribution of the core resin particle D5-dispersed liquid are illustrated in FIG. 1.

B. Coating the Surfaces of the Core Resin Particles which Form the Core Portion with a Resin Including an Organic Ultraviolet Absorbent Methyl methacrylate (38.5 parts by mass) and a phosphate ester-type surfactant (1.5 parts by mass) were mixed, subsequently, avobenzone (Parsol 1789 (registered trademark), 10.0 parts by mass) was added, and fully dissolved, thereby obtaining an organic ultraviolet absorbent-containing MMA-dissolved liquid.

Next, the organic ultraviolet absorbent-containing MMA-dissolved liquid (42.0 parts by mass) and a potassium persulfate-dissolved liquid including potassium persulfate (0.098 parts by mass) dissolved in pure water (97.902 parts by mass) were mixed, and emulsified using a homogenizer, thereby obtaining a coated resin-emulsified liquid.

Next, the coated resin-emulsified liquid (140 parts by mass) and the core resin particle-dispersed liquid (400 parts by mass) were mixed, substituted by nitrogen at room temperature (25° C.) for 1 hour, heated and held at 65° C. for 3 hours, thereby causing a polymerization reaction. Next, the obtained reaction liquid was cooled using ice so as to stop the polymerization reaction, the obtained polymerized substance was washed using pure water, and then dried at 90° C. After that, the dried substance was cracked using a hammer mill, thereby obtaining a zinc oxide-containing core shell-type ultraviolet-shielding agent of Example 1.

When the respective content rates of zinc oxide and the organic ultraviolet absorbent in the zinc oxide-containing core shell-type ultraviolet-shielding agent are computed based on the respective parts by mass of the coated resin-emulsified liquid and the core resin particle-dispersed liquid during the mixing, the content rate of zinc oxide is 35% by mass, and the content rate of the organic ultraviolet absorbent is 6% by mass.

"Evaluation of the Core Shell-Type Ultraviolet-Shielding Agent"

A. Measurement of the Average Long Diameter

Figure 2:
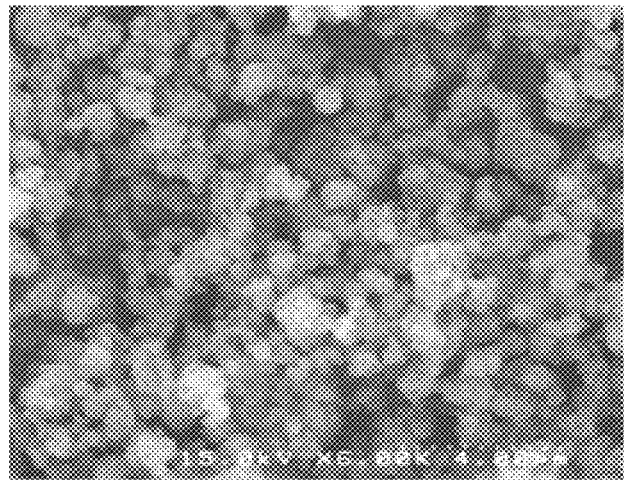
FIG. 2 is a scanning electron microscopic (SEM) image illustrating a core shell-type ultraviolet-shielding agent of Example 1 of the invention.
Figure 3:
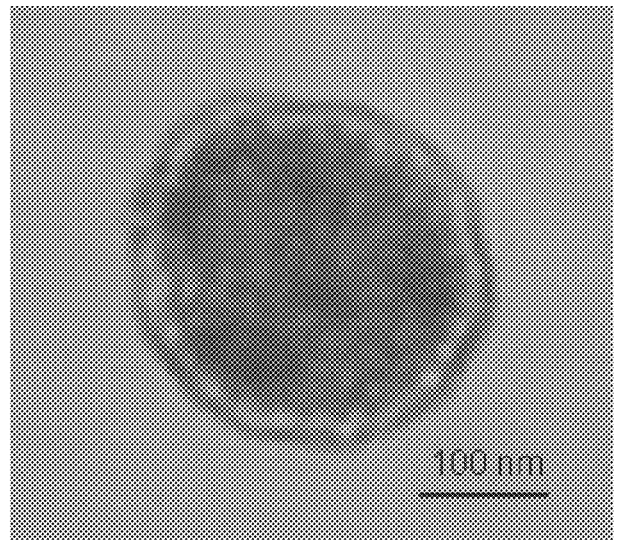
FIG. 3 is a transmission electron microscopic (TEM) image illustrating the core shell-type ultraviolet-shielding agent of Example 1 of the invention.

The scanning electron microscopic (SEM) image and transmission electron microscopic (TEM) image of the core shell-type ultraviolet-shielding agent are illustrated in FIGS. 2 and 3 respectively.

As a result of measuring the particle diameters of 100 particles in the core shell-type ultraviolet-shielding agent in the SEM image of FIG. 2, the particle diameters were in a range of 0.1 μm to 0.5 μm, and the average particle diameter was 0.25 μm. In addition, from the TEM image of FIG. 3, it was confirmed that the core particles were coated with a 0.02 μm-thick resin containing the organic ultraviolet absorbent.

B. Measurement of Residual Monomers

Regarding vapor-phase parts generated by sealing the core shell-type ultraviolet-shielding agent (0.5 parts by mass) in a 22 mL heat-resistant container (headspace vials), and heating the core shell-type ultraviolet-shielding agent at 150° C. for 40 minutes, the quantity of methyl methacrylate monomers remaining in the core shell-type ultraviolet-shielding agent was measured using a mass analyzer gas chromatography GC-MS.

The multiple headspace extraction (MHE) method, which is a multi-step heating and extraction method, was used as a method for measuring the quantity of the residual monomers.

As a result, the amount of the methyl methacrylate monomers remaining in the core shell-type ultraviolet-shielding agent was 3.4 ppm.

Next, the zinc oxide-containing core shell-type ultraviolet-shielding agent (60 parts by mass), decamethylcyclopentasiloxane (D5) SH245 (manufactured by Dow Corning Toray Co., Ltd., 51 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core shell-type ultraviolet-shielding agent-containing dispersion liquid of Example 1 containing 50% by mass of a zinc oxide-containing core shell-type ultraviolet-shielding agent.

Figure 4:
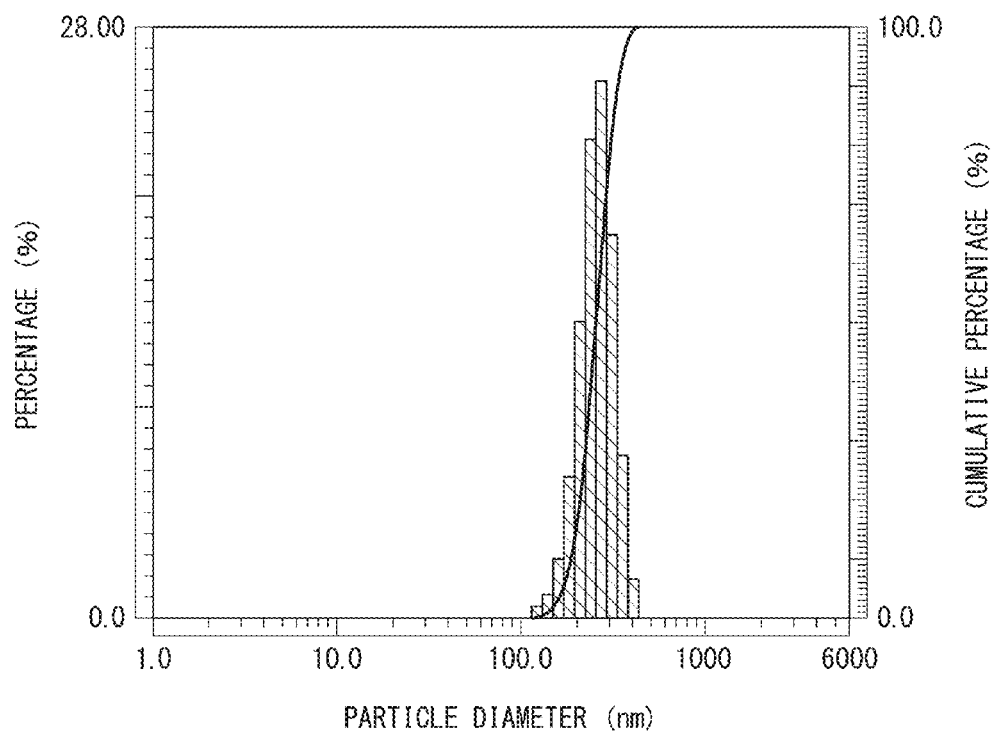
FIG. 4 is a view illustrating the volume particle size distribution and cumulative volume particle size distribution of a core shell-type ultraviolet-shielding agent-containing dispersion liquid of Example 1 of the invention.

Next, the obtained core shell-type ultraviolet-shielding agent-containing dispersion liquid is diluted by adding D5 so that the core shell-type ultraviolet-shielding agent became 10% by mass, the dispersed particle diameters of fine core shell-type zinc oxide particles in the diluted liquid were measured using a dynamic light scattering particle size distribution measurement apparatus LB-550 (manufactured by Horiba, Ltd.), and the volume particle size distribution and cumulative volume particle size distribution were computed. As a result, the particle diameter at the 10 volume % point (D10) in the cumulative volume particle size distribution was 194.6 nm, the particle diameter at the 50 volume % point (D50) was 262.6 nm, and the particle diameter at the 90 volume % point (D90) was 338.0 nm. The volume particle size distribution and cumulative volume particle size distribution of the core shell-type ultraviolet-shielding agent-containing dispersion liquid are illustrated in FIG. 4.

"Measurement of Spectral Transmittance and SPF"

The core shell-type ultraviolet-shielding agent-containing dispersion liquid was coated on a silica sheet with an appropriate adjustment using a wire bar so as to form a desired film thickness, thereby manufacturing a coated film (measurement specimen). Here, five measurement specimens having film thicknesses of 5 μm, 8 μm, 10 μm, 18 μm and 25 μm were manufactured.

Figure 5:
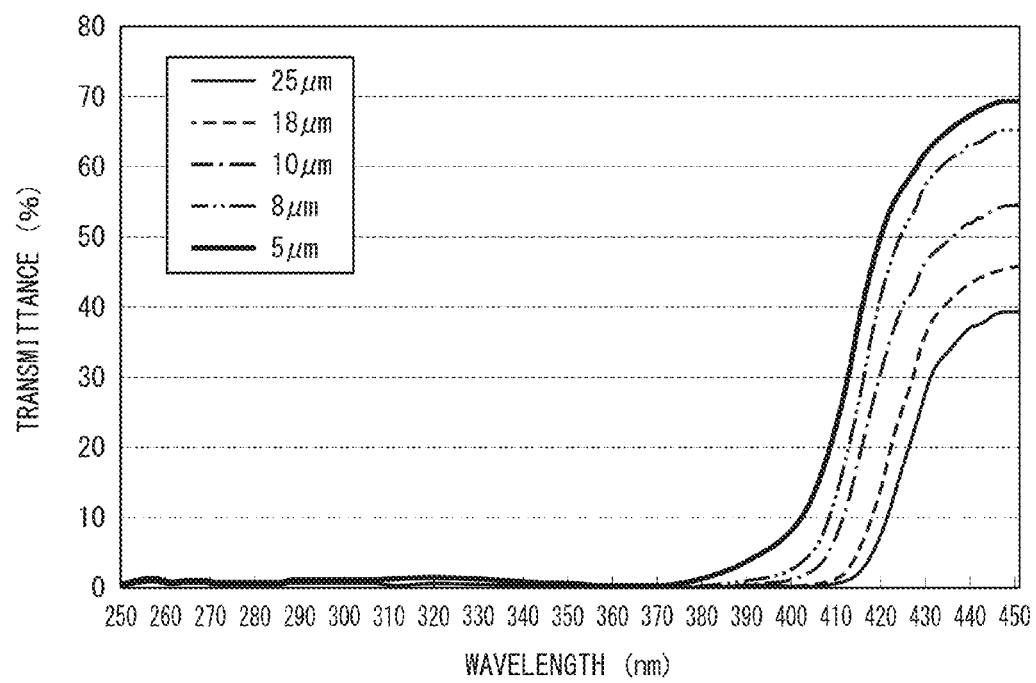
FIG. 5 is a view illustrating a spectral transmittance of a coated film (measurement specimen) obtained in Example 1 of the invention.

Next, the spectral transmittances and SPF values of the five coated films were measured respectively using an SPF analyzer UV-1000S (manufactured by Labsphere, Inc.). The graph of the obtained spectral transmittances is illustrated in FIG. 5. From FIG. 5, it was confirmed that ultraviolet rays of near 400 nm were shielded in all film thicknesses.

In addition, the SPF values of the core shell-type ultraviolet-shielding agent-containing dispersion liquid were 158 at the thickness of 5 μm, 244 at the thickness of 8 μm, 339 μm at the thickness of 10 μm, 357 at the thickness of 18 μm and 381 at the thickness of 25 μm.

"Manufacturing of the Core Shell-Type Ultraviolet-Shielding Agent-Containing Water Dispersion Liquid"

Next, the zinc oxide-containing core shell-type ultraviolet-shielding agent (20 parts by mass), ethanol (7.5 parts by mass) and pure water (22.5 parts by mass) were mixed, thereby obtaining a core shell-type ultraviolet-shielding agent-containing water dispersion liquid including 40% by mass of the core shell-type ultraviolet-shielding agent.

"Manufacturing of a Moisture Gel"

Next, the core shell-type ultraviolet-shielding agent-containing water dispersion liquid (25 parts by mass), sodium carboxymethyl cellulose (1.5 parts by mass), ethanol (6.25 parts by mass), glycerin (2.5 parts by mass) and pure water (14.75 parts by mass) were mixed, and stirred at 70° C. for 10 minutes, thereby obtaining a moisture gel including 20% by mass of the core shell-type ultraviolet-shielding agent.

Comparative Example 1

The core resin particles (20 parts by mass) obtained in Example 1, ethanol (7.5 parts by mass) and pure water (22.5 parts by mass) were mixed, thereby obtaining a core resin particle-containing water dispersion liquid including 40% by mass of the core resin particles.

A moisture gel including 20% by mass of the core resin particles was obtained using the core resin particle-containing water dispersion liquid in the same manner as in Example 1.

Comparative Example 2

Avobenzone (Parsol 1789 (registered trademark), 24 parts by mass) was added to methyl methacrylate (96 parts by mass), and fully dissolved, thereby obtaining an organic ultraviolet absorbent-containing MMA-dissolved liquid.

Next, the organic ultraviolet absorbent-containing MMA-dissolved liquid (100 parts by mass), a phosphate ester-type surfactant (5 parts by mass), pure water (229.5 parts by mass), sodium dodecylbenzenesulfonate (0.5 parts by mass), ethylene glycol dimethacrylate (14.0 parts by mass) and a silicone-based defoamer (1.0 parts by mass) were mixed and stirred using a homogenizer, thereby obtaining an emulsion.

Next, the emulsion (320 parts by mass), pure water (79.856 parts by mass) and potassium persulfate (0.144 parts by mass) were mixed, moved to a reaction apparatus equipped with a stirrer and a thermometer, and substituted by nitrogen at room temperature (25° C.) for 1 hour. Next, the emulsion was heated and held at 65° C. for 3 hours so as to cause a polymerization reaction. Next, the obtained reaction liquid was cooled using ice so as to stop the polymerization reaction, the obtained polymerized substance was washed using pure water, and then dried at 90° C. After that, the dried substance was cracked using a hammer mill, thereby obtaining an ultraviolet-shielding agent configured only of core resin particles containing an organic ultraviolet absorbent.

When the content rate of the organic ultraviolet absorbent in the core resin particles in the emulsion is computed based on the parts by mass of the emulsion during the mixing, the content rate is 20% by mass.

Next, the ultraviolet-shielding agent (20 parts by mass) configured only of core resin particles containing the organic ultraviolet absorbent, ethanol (7.5 parts by mass) and pure water (22.5 parts by mass) were mixed, thereby obtaining an ultraviolet absorbent-containing core resin particle water dispersion liquid which includes 40% by mass of the core resin particles containing the organic ultraviolet absorbent.

A moisture gel including 20% by mass of the ultraviolet absorbent-containing core resin particles was obtained using the ultraviolet absorbent-containing core resin particle water dispersion liquid in the same manner as in Example 1.

"Evaluation of the Moisture Gels"

Figure 6:
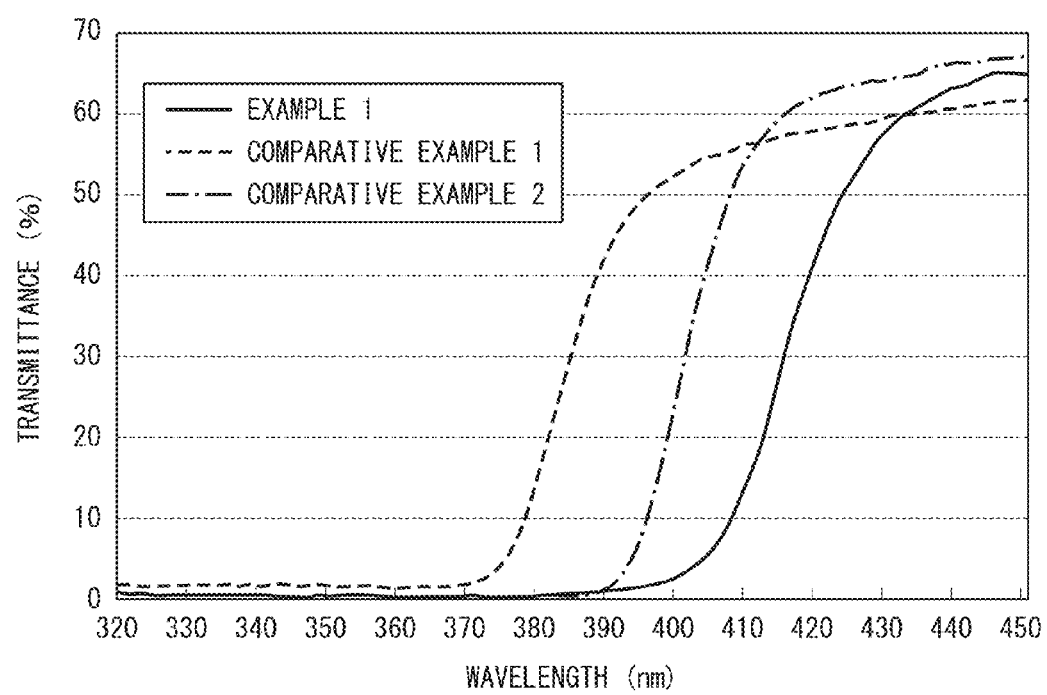
FIG. 6 is a view illustrating spectral transmittances of moisture gels of Example 1 and Comparative Examples 1 and 2 of the invention.

Each of the moisture gels of Example 1 and Comparative Examples 1 and 2 was coated on a silica sheet in an amount of 2 mg/cm², and the spectral transmittance and SPF value were measured using an SPF analyzer UV-1000S (manufactured by Labsphere, Inc.). The graph of the obtained spectral transmittances is illustrated in FIG. 6. From FIG. 6, it was confirmed that, since including the core shell-type ultraviolet-shielding agent, the moisture gel of Example 1 was excellent in terms of transparency in the visible light range and further shielded ultraviolet rays of 400 nm or less compared with the moisture gels of Comparative Examples 1 and 2.

In addition, the SPF value of the moisture gel of Example 1 was 244, the SPF value of the moisture gel of Comparative Example 1 was 33, and the SPF value of the moisture gel of Comparative Example 2 was 40.

Example 2

Manufacturing of a Sunscreen Agent

The following components were blended at the following formulation, and well mixed, thereby obtaining a sunscreen agent.

| | |
|---|---|
| The core shell-type ultraviolet-shielding agent-containing dispersion liquid of Example 1 | 60 parts by mass |
| Silicone resin SH3775M (manufactured by Dow Corning Toray Co., Ltd.) | 2.0 parts by mass |
| Silicone elastomer "TORAYFIL E-508" (manufactured by Dow Corning Toray Co., Ltd.) | 5.0 parts by mass |
| Ethanol | 10 parts by mass |
| Trifluoropropylated dimethiconol gum | 35 parts by mass |
| Methyl trimethicone solution | 1.0 part by mass |
| Poly alkyl silsesquioxane | 0.5 parts by mass |
| Methyl phenyl polysiloxane | 4.0 parts by mass |
| Purified water | 14 parts by mass |
| Preservative | appropriate amount |
| Decamethylcyclopentasiloxane (D5) SH245 | remainder |

Here, ethanol was mixed with purified water in advance so as to manufacture a water-phase component, other components were mixed so as to manufacture an oil-phase component, the water-phase component was added to the oil-phase component, and well mixed, thereby obtaining a sunscreen agent of Example 2 containing 20% by mass of a core shell-type ultraviolet-shielding agent containing zinc oxide particles.

Comparative Example 3

Fine zinc oxide particles ZnO-350 (primary particle diameter 25 nm) (manufactured by Sumitomo Osaka Cement Company, Limited, 60 parts by mass), decamethyl cyclopentasiloxane (D5) SH245 (manufactured by Dow Corning Toray Co., Ltd., 51 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a zinc oxide-containing dispersion liquid containing 50% by mass of fine zinc oxide particles.

Next, the following components were blended at the following formulation, and well mixed, thereby obtaining a sunscreen agent.

| | |
|---|---|
| The zinc oxide-containing dispersion liquid | 60 parts by mass |
| Silicone resin SH3775M (manufactured by Dow Corning Toray Co., Ltd.) | 2.0 parts by mass |
| Silicone elastomer "TORAYFIL E-508" (manufactured by Dow Corning Toray Co., Ltd.) | 5.0 parts by mass |
| Ethanol | 10 parts by mass |
| Trifluoropropylated dimethiconol gum | 35 parts by mass |
| Methyl trimethicone solution | 1.0 part by mass |
| Poly alkyl silsesquioxane | 0.5 parts by mass |
| Methyl phenyl polysiloxane | 4.0 parts by mass |
| Purified water | 14 parts by mass |
| Preservative | appropriate amount |
| Decamethylcyclopentasiloxane (D5) SH245 | remainder |

"Evaluation of the Sunscreen Agents"

Figure 7:
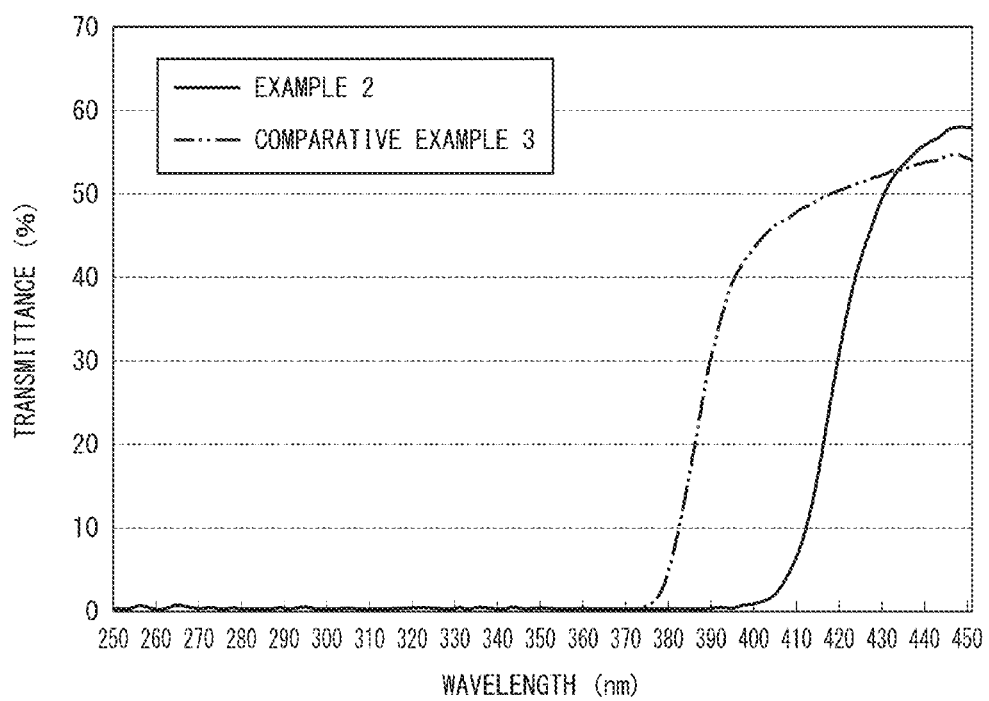
FIG. 7 is a view illustrating spectral transmittances of sunscreen agents of Example 2 and Comparative Example 3 of the invention.

Each of the sunscreen agents of Example 2 and Comparative Example 3 was coated on a silica sheet in an amount of 2 mg/cm², and the spectral transmittance and SPF value were measured using an SPF analyzer UV-1000S (manufactured by Labsphere, Inc.). The graph of the obtained spectral transmittances is illustrated in FIG. 7. From FIG. 7, it was confirmed that, since including the core shell-type ultraviolet-shielding agent, the sunscreen agent of Example 2 shielded ultraviolet rays of 400 nm or less. On the other hand, it was confirmed that the sunscreen agent of Comparative Example 3 could only shield ultraviolet rays of 380 nm or less.

In addition, the SPF value of the sunscreen agent of Example 2 was 343, and the SPF value of the sunscreen agent of Comparative Example 3 was 35.

"Evaluation of the Skin Coatability of the Sunscreen Agents"

The skin coatability of the sunscreen agents of Example 2 and Comparative Example 3 was evaluated.

Here, 20 panelists were selected, each of the panelists determined the respective evaluation items of "feeling in use" and "transparency" to be excellent or poor, the number of panelists who had determined the respective evaluation items to be excellent was computed, and the skin coatability was evaluated based on the number of panelists using the following rates.

Number of panelists out of 20 who answered "excellent"

|  | Evaluation |
| --- | --- |
| 15 panelists to 20 panelists | "A" |
| 10 panelists to 14 panelists | "B" |
| 5 panelists to 9 panelists | "C" |
| 0 panelists to 4 panelists | "D" |

The evaluation results showed that the sunscreen agent of Example 2 was "A" for both the feeling in use and the transparency, but the sunscreen agent of Comparative Example 3 was "B" for the feeling in use and "C" for the transparency.

Example 3

A core shell-type ultraviolet-shielding agent containing titanium oxide particles was obtained in the same manner as in Example 1 except that titanium oxide (average primary particle diameter: 0.03 μm, manufactured by Ishihara Sangyo Kaisha, Ltd.) was used instead of zinc oxide in Example 1.

Next, the following components were blended at the following formulation, thereby manufacturing a foundation.

| | |
| --- | --- |
| Bengala | 1.0 part by mass |
| Iron oxide (yellow) | 3.3 parts by mass |
| Iron oxide (red) | 0.9 parts by mass |
| Iron oxide (black) | 0.3 parts by mass |
| The titanium oxide particle-containing core shell-type ultraviolet-shielding agent | 45.0 parts by mass |
| Sericite | 13.5 parts by mass |
| Liquid paraffin | 3.0 parts by mass |
| Tri(capryl-caprylic acid)glycerin | 5.0 parts by mass |
| Isoparaffin wax | 3.0 parts by mass |
| Dimethyl polysiloxane | 3.0 parts by mass |
| Preservative | appropriate amount |
| Talc | remainder |

Here, in the above formulation, a substance obtained by heating and mixing in an oil component was added little by little and well mixed with a previously mixed powder component, and then loaded into a mold, thereby obtaining a foundation.

Example 4

Next, the following components were blended at the following formulation.

| | |
| --- | --- |
| Bengala | 1.0 part by mass |
| Iron oxide (yellow) | 3.3 parts by mass |
| Iron oxide (red) | 0.9 parts by mass |
| Iron oxide (black) | 0.3 parts by mass |
| The zinc oxide-containing core shell-type ultraviolet-shielding agent of Example 1 | 45.0 parts by mass |
| Sericite | 13.5 parts by mass |
| Liquid paraffin | 3.0 parts by mass |
| Tri(capryl-caprylic acid)glycerin | 5.0 parts by mass |
| Isoparaffin wax | 3.0 parts by mass |
| Dimethyl polysiloxane | 3.0 parts by mass |
| Preservative | appropriate amount |
| Talc | remainder |

Here, in the above formulation, a substance obtained by heating and mixing in an oil component was added little by little and well mixed with a previously mixed powder component, and then loaded into a mold, thereby obtaining a foundation.

Comparative Example 4

The following components were blended at the following formulation.

A mixture (VT) obtained by blending the ultraviolet-shielding agent of Comparative Example 2 and titanium oxide TTO-51 (manufactured by Ishihara Sangyo Kaisha, Ltd.) at a mass ratio of 1:1 was used as an ultraviolet-shielding agent.

| | |
| --- | --- |
| Bengala | 1.0 part by mass |
| Iron oxide (yellow) | 3.3 parts by mass |
| Iron oxide (red) | 0.9 parts by mass |
| Iron oxide (black) | 0.3 parts by mass |
| The mixture (VT) | 45.0 parts by mass |
| Sericite | 13.5 parts by mass |
| Liquid paraffin | 3.0 parts by mass |
| Tri(capryl-caprylic acid)glycerin | 5.0 parts by mass |
| Isoparaffin wax | 3.0 parts by mass |
| Dimethyl polysiloxane | 3.0 parts by mass |
| Preservative | appropriate amount |
| Talc | remainder |

Here, in the above formulation, a substance obtained by heating and mixing in an oil component was added little by little and well mixed with a previously mixed powder component, and then loaded into a mold, thereby obtaining a foundation.

"Evaluation of the Skin Coatability of the Foundations"

The skin coatability of the foundations of Examples 3 and 4 and Comparative Example 4 was evaluated in the same manner as in the evaluation of the skin coatability of the sunscreen agents.

As a result, the foundation of Example 3 was "A" for both the feeling in use and the wrinkle-hiding effect, and the foundation of Example 4 was "A" for the feeling in use and "B" for the wrinkle-hiding effect. On the other hand, the foundation of Comparative Example 4 was "C" for both the feeling in use and the wrinkle-hiding effect.

Generally, titanium oxide is superior to zinc oxide in terms of the wrinkle-hiding effect due to its scattering effect.

Here, a foundation for which the zinc oxide-containing core shell-type ultraviolet-shielding agent of Example 4 was used was compared with a foundation for which the titanium oxide of Comparative Example 4 was used in a particle form, and the result was that the foundation for which the zinc oxide-containing core shell-type ultraviolet-shielding agent of Example 4 was used was excellent in terms of the wrinkle-hiding effect. This is considered to be because zinc oxide is included in the resin so that the shading effect is enhanced due to the scattering effects of the resin and zinc oxide.

Example 5

The core shell-type ultraviolet-shielding agent including fine zinc oxide particles obtained in Example 1 (36 parts by mass), decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core shell-type ultraviolet-shielding agent-containing dispersion liquid of Example 5 which includes 30% by mass of the core shell-type ultraviolet-shielding agent containing fine zinc oxide particles.

Next, the dispersed particle diameters of the fine core shell-type zinc oxide particles in the obtained core shell-type ultraviolet-shielding agent-containing dispersion liquid were measured according to Example 1. As a result, the particle diameter at the 10 volume % point (D10) in the cumulative volume particle size distribution was 194.6 nm, the particle diameter at the 50 volume % point (D50) was 262.6 nm, and the particle diameter at the 90 volume % point (D90) was 338.0 nm.

Next, the following components were blended at the following formulation.

| | |
|---|---|
| The core shell-type ultraviolet-shielding agent-containing dispersion liquid | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent of Example 5 containing 20% by mass of a core shell-type ultraviolet-shielding agent containing zinc oxide particles.

Comparative Example 5

Fine zinc oxide particles ZnO-350 (primary particle diameter 25 nm) (manufactured by Sumitomo Osaka Cement Company, Limited, 36 parts by mass), decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a zinc oxide-containing dispersion liquid of Comparative Example 5 containing 30% by mass of fine zinc oxide particles.

Next, the following components were blended at the following formulation.

| | |
|---|---|
| The zinc oxide-containing dispersion liquid | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent.

Example 6

Manufacturing of a Core Shell-Type Ultraviolet-Shielding Agent

A. Manufacturing of a Core Resin Particle-Dispersed Liquid Containing an Organic Ultraviolet Absorbent-Containing Resin which Forms the Core Portion Methyl methacrylate (84.7 parts by mass) and a phosphate ester-type surfactant (3.3 parts by mass) were mixed, subsequently, avobenzone (Parsol 1789 (registered trademark), 22 parts by mass) was added, and fully dissolved, thereby obtaining an organic ultraviolet absorbent-containing MMA-dissolved liquid.

Next, the organic ultraviolet absorbent-containing MMA-dispersed liquid (105.0 parts by mass), pure water (229.5 parts by mass), sodium dodecylbenzenesulfonate (0.5 parts by mass), ethylene glycol dimethacrylate (14.0 Parts by mass) and a silicone-based defoamer (1.0 parts by mass) were mixed and stirred using a homogenizer, thereby obtaining an emulsion.

Next, the obtained emulsion (320.0 parts by mass), pure water (79.856 parts by mass) and potassium persulfate (0.144 parts by mass) were mixed, moved to a reaction apparatus equipped with a stirrer and a thermometer, and substituted by nitrogen at room temperature for 1 hour. Next, the emulsion was heated and held at 65° C. for 3 hours so as to cause a polymerization reaction.

Next, the reaction liquid was cooled using ice so as to stop the polymerization reaction, thereby obtaining a core resin particle-dispersed liquid containing the organic ultraviolet absorbent.

B. Coating the Organic Ultraviolet Absorbent-Containing Resin which Forms the Core Portion with a Fine Zinc Oxide Particle-Containing Resin Fine zinc oxide particles having an average primary particle diameter of 0.02 μm (manufactured by Sumitomo Osaka Cement Company, Limited, 200 parts by mass), methyl methacrylate (188 parts by mass) and a phosphate ester-type surfactant (12 parts by mass) were mixed and dispersed using a sand mill for 2 hours, thereby obtaining a monomer (MMA)-dispersed liquid including fine zinc oxide particles dispersed in methyl methacrylate.

Next, the monomer (MMA)-dispersed liquid (105.0 parts by mass), pure water (229.27 parts by mass), potassium persulfate (0.23 parts by mass), sodium dodecylbenzenesulfonate (0.5 parts by mass), ethylene glycol dimethacrylate (14.0 Parts by mass) and a silicone-based defoamer (1.0 parts by mass) were mixed and stirred using a homogenizer, thereby obtaining an emulsion.

Next, the obtained emulsion (140 parts by mass) and the core resin particle-dispersed liquid (250 parts by mass) containing the organic ultraviolet absorbent were mixed, substituted by nitrogen at room temperature (25° C.) for 1 hour, heated and held at 65° C. for 3 hours, thereby causing a polymerization reaction. Next, the obtained reaction liquid was cooled using ice so as to stop the polymerization reaction, the obtained polymerized substance was washed using pure water, and then dried at 90° C. After that, the dried substance was cracked using a hammer mill, thereby obtaining a core shell-type ultraviolet-shielding agent of Example 6.

When the respective content rates of zinc oxide and the organic ultraviolet absorbent in the core shell-type ultraviolet-shielding agent are computed based on the respective parts by mass of the emulsion and the core resin particle-dispersed liquid during the mixing, the content rate of zinc oxide is 21% by mass, and the content rate of the organic ultraviolet absorbent is 12% by mass.

Next, the obtained core shell-type ultraviolet-shielding agent (36 parts by mass), decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core shell-type ultraviolet-shielding agent-containing dispersion liquid of Example 6 which includes 30% by mass of the core shell-type ultraviolet-shielding agent.

Figure 8:
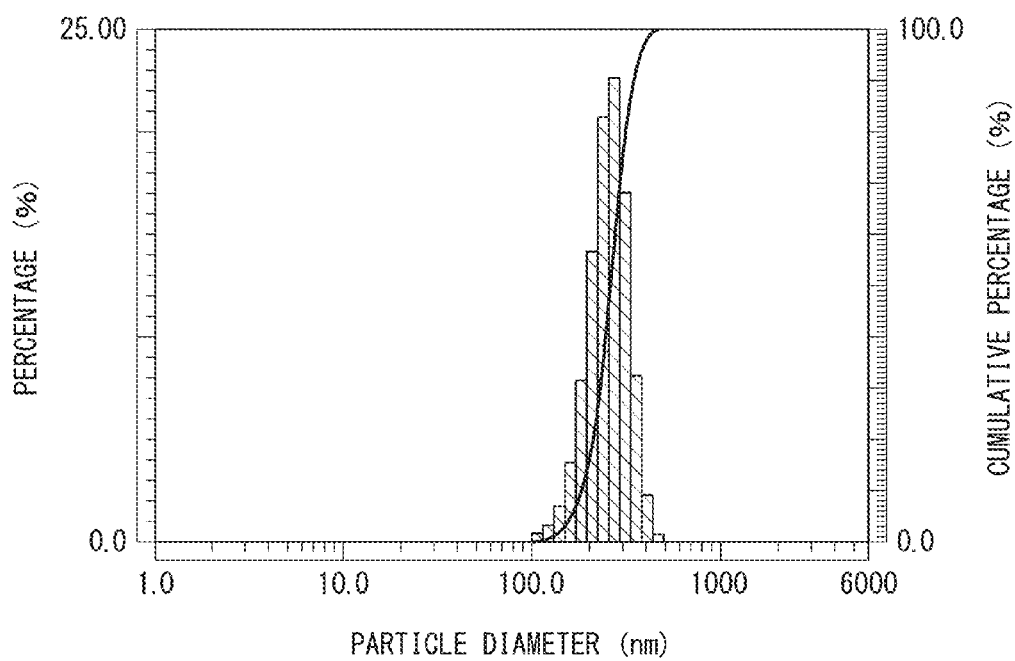
FIG. 8 is a view illustrating the volume particle size distribution and cumulative volume particle size distribution of a core shell-type ultraviolet-shielding agent-containing dispersion liquid of Example 6 of the invention.

Next, as a result of measuring the dispersed particle diameters of the core shell-type ultraviolet-shielding agent in the core shell-type ultraviolet-shielding agent-containing dispersion liquid according to Example 1, the particle diameter at the 10 volume % point (D10) in the cumulative volume particle size distribution was 181.5 nm, the particle diameter at the 50 volume % point (D50) was 259.2 nm, and the particle diameter at the 90 volume % point (D90) was 343.9 nm. The volume particle size distribution and cumulative volume particle size distribution of the core shell-type ultraviolet-shielding agent-containing dispersion liquid are illustrated in FIG. 8.

Next, the components were blended at the following formulation.

| | |
|---|---|
| The core shell-type ultraviolet-shielding agent-containing dispersion liquid | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent of Example 6 containing 20% by mass of the core shell-type ultraviolet-shielding agent.

"Evaluation of the Sunscreen Agents"

Each of the sunscreen agents of Examples 5 and 6 and Comparative Example 5 was coated on a silica sheet in an amount of 2 mg/cm$^2$, and the spectral transmittance and SPF value were measured using an SPF analyzer UV-1000S (manufactured by Labsphere, Inc.).

Figure 9:
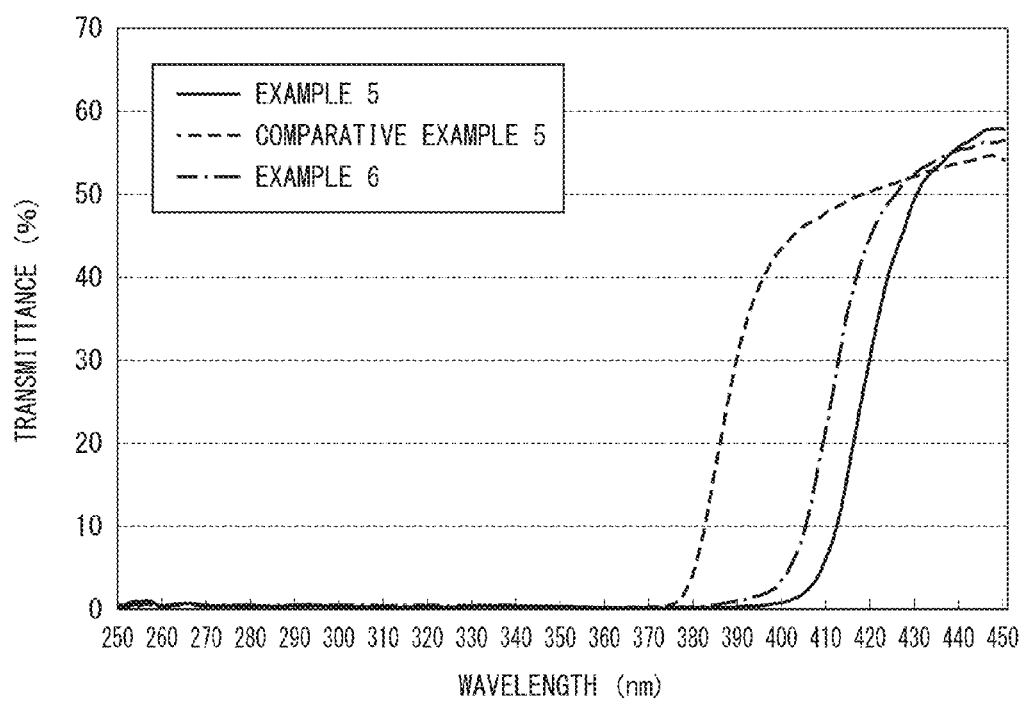
FIG. 9 is a view illustrating spectral transmittances of sunscreen agents of Examples 5 and 6 and Comparative Example 5 of the invention.

As a result, the SPF value of the sunscreen agent of Example 5 was 343.3, the SPF value of the sunscreen agent of Example 6 was 188.7, and the SPF value of the sunscreen agent of Comparative Example 5 was 34.8. FIG. 9 illustrates the spectral transmittances of Examples 5 and 6 and Comparative Example 5.

From FIG. 9, it was confirmed that the sunscreen agent of Example 5 shielded ultraviolet rays of 400 nm or less, and, furthermore, substantially shielded ultraviolet rays of 390 nm or less.

It was confirmed that the sunscreen agent of Example 6 had a strong ultraviolet-shielding effect near 400 nm, and, furthermore, substantially shielded ultraviolet rays of 380 nm or less.

When the sunscreen agent of Example 5 is compared with the sunscreen agent of Example 6, the sunscreen agent of Example 5 has a superior ultraviolet-shielding effect, which is considered to be because avobenzone is present in the shell portion so that avobenzone is locally concentrated.

Meanwhile, it was confirmed that the sunscreen agent of Comparative Example 5, unlike the sunscreen agents of Examples 5 and 6, failed to produce the ultraviolet-shielding effect near 400 nm, and could shield only ultraviolet rays of 380 nm or less.

Example 7

A core shell-type ultraviolet-shielding agent containing titanium oxide particles was obtained in the same manner as in Example 1 except that titanium oxide (average primary particle diameter: 0.03 μm, manufactured by Ishihara Sangyo Kaisha, Ltd.) was used instead of zinc oxide.

When the respective content rates of titanium oxide and the organic ultraviolet absorbent in the titanium oxide-containing core shell-type ultraviolet-shielding agent are computed based on the parts by mass during the mixing, the content rate of titanium oxide is 35% by mass, and the content rate of the organic ultraviolet absorbent is 6% by mass.

Next, the core shell-type ultraviolet-shielding agent (36 parts by mass) containing titanium oxide particles, decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core shell-type ultraviolet-shielding agent-containing dispersion liquid of Example 7 which includes 30% by mass of the core shell-type ultraviolet-shielding agent containing titanium oxide particles.

Figure 10:
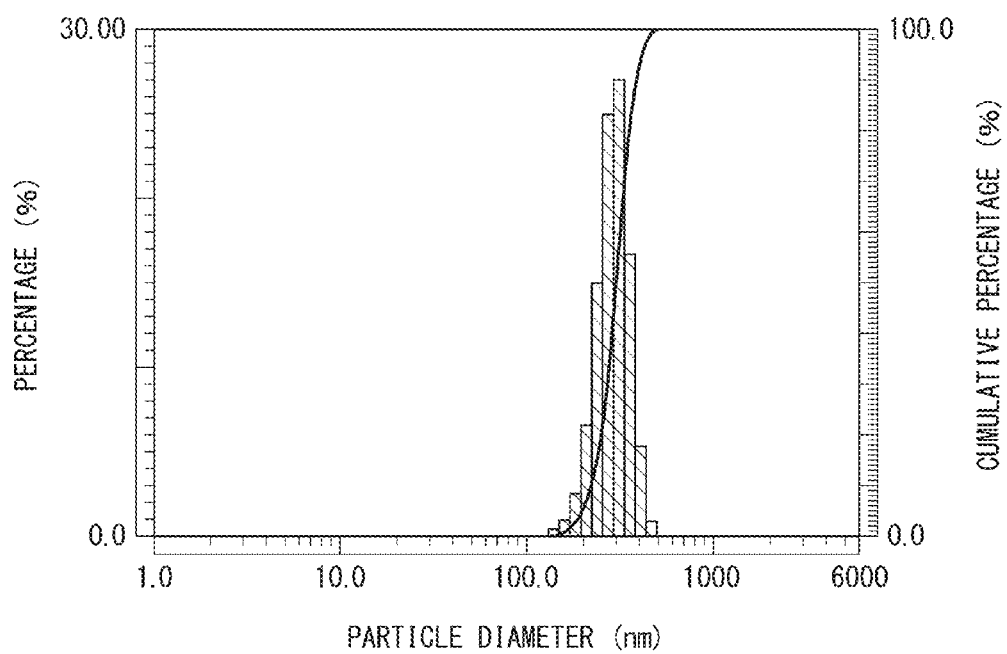
FIG. 10 is a view illustrating the volume particle size distribution and cumulative volume particle size distribution of a core shell-type ultraviolet-shielding agent-containing dispersion liquid of Example 7 of the invention.

Next, the dispersed particle diameters of the core shell-type titanium oxide particles in the obtained core shell-type ultraviolet-shielding agent-containing dispersion liquid were measured according to Example 1. As a result, the particle diameter at the 10 volume % point (D10) in the cumulative volume particle size distribution was 225.1 nm, the particle diameter at the 50 volume % point (D50) was 295.9 nm, and the particle diameter at the 90 volume % point (D90) was 376.6 nm. The volume particle size distribution and cumulative volume particle size distribution of the core shell-type ultraviolet-shielding agent-containing dispersion liquid are illustrated in FIG. 10.

Next, the following components were blended at the following formulation.

| | |
|---|---|
| The core shell-type ultraviolet-shielding agent-containing dispersion liquid containing titanium oxide particles | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent of Example 7 containing 20% by mass of the core shell-type ultraviolet-shielding agent that contains titanium oxide particle.

Comparative Example 6

Fine titanium oxide particles (average primary particle diameter: 0.03 μm) (manufactured by Ishihara Sangyo Kaisha, Ltd., 36 parts by mass), decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a fine titanium oxide particle-containing dispersion liquid of [Comparative Example 6 containing 30% by mass of fine titanium oxide particles.

Next, the following components were blended at the following formulation.

| | |
|---|---|
| The fine titanium oxide particle-containing dispersion liquid | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent of Comparative Example 6 containing 20% by mass of fine titanium oxide particles.

"Evaluation of the Sunscreen Agents"

Each of the sunscreen agents of Example 7 and Comparative Example 6 was coated on a silica sheet in an amount of 2 mg/cm$^2$, and the spectral transmittance and SPF value were measured using an SPF analyzer UV-1000S (manufactured by Labsphere, Inc.).

Figure 11:
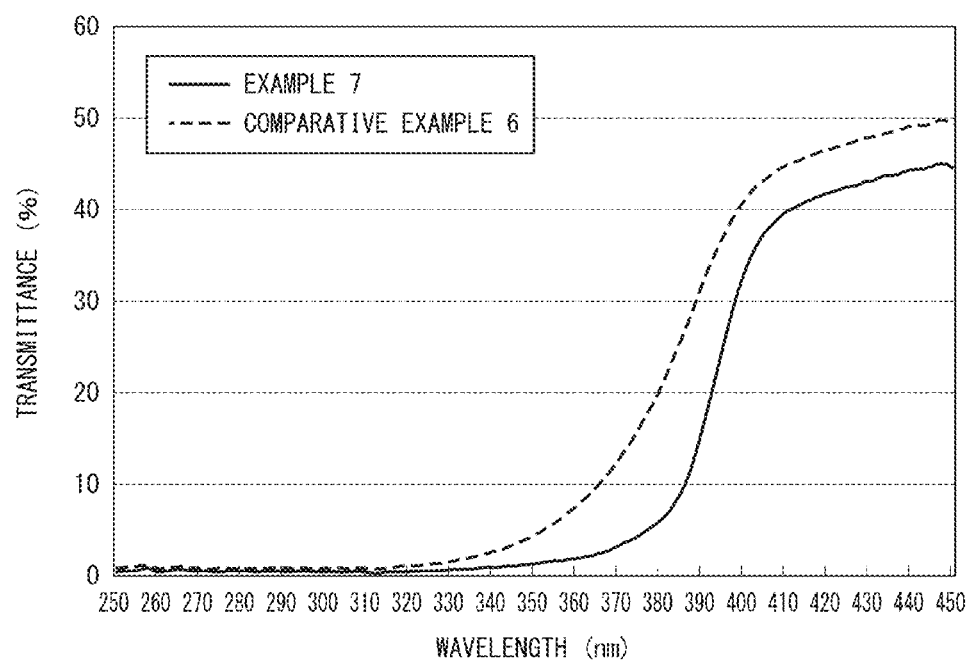
FIG. 11 is a view illustrating spectral transmittances of sunscreen agents of Example 7 and Comparative Example 6 of the invention.

As a result, the SPF value of the sunscreen agent of Example 7 was 145.2, and the SPF value of the sunscreen agent of Comparative Example 6 was 63.6. FIG. 11 illustrates the spectral transmittances of Example 7 and Comparative Example 6.

From FIG. 11, it was confirmed that the sunscreen agent of Example 7 further shielded ultraviolet rays on the long wavelength side compared with the sunscreen agent of Comparative Example 6.

"Evaluation of the Skin Coatability of the Sunscreen Agents"

The skin coatability of the sunscreen agents of Examples to 7 and Comparative Examples 5 and 6 was evaluated.

Here, 20 panelists were selected, each of the panelists determined the respective evaluation items of "feeling in use" and "transparency" to be excellent or poor, the number of panelists who had determined the respective evaluation items to be excellent was computed, and the skin coatability was evaluated based on the number of panelists using the following rates.

Number of panelists out of 20 who answered "excellent"

| Evaluation | |
|---|---|
| 15 panelists to 20 panelists | "A" |
| 10 panelists to 14 panelists | "B" |
| 5 panelists to 9 panelists | "C" |
| 0 panelists to 4 panelists | "D" |

The evaluation results showed that the sunscreen agents of Examples 5 to 7 were "A" for both the feeling in use and the transparency, but the sunscreen agents of Comparative Examples 5 and 6 were "B" for the feeling in use and "C" for the transparency.

This is considered to be because, when formed in the core shell structure, the sunscreen agent is easily spread on skin, and fine metallic oxide particles are prevented from aggregating and the like.

Comparative Example 7

Avobenzone was dissolved in decamethyl cyclopentasiloxane (D5) SH245 (manufactured by Dow Corning Toray Co., Ltd.) at 80° C., thereby obtaining an avobenzone-containing D5-dispersed liquid containing 1.8% by mass of avobenzone.

Next, the following components were blended at the following formulation.

| | |
|---|---|
| The avobenzone-containing D5-dispersed liquid | 66.8 parts by mass |
| Film-forming agent: linear polyether-denatured silicone (KF6028, manufactured by Shin-Etsu Chemical Co., Ltd.) | 9.6 parts by mass |
| Emulsifier: branched polyether-denatured silicone (KF6017, manufactured by Shin-Etsu Chemical Co., Ltd.) | 10.4 parts by mass |
| 1,3-butanediol | 5.0 parts by mass |
| Purified water | 8.2 parts by mass |

Here, a water-phase component was manufactured by mixing 1,3-butanediol with purified water in advance, other components were mixed so as to manufacture an oil-phase component, the water-phase component was added to the oil-phase component, and well mixed, thereby obtaining a sunscreen agent of Comparative Example 7.

"Photostability Test"

Each of the sunscreen agents of Example 5 and Comparative Example 7 was coated on a silica sheet using a wire bar #8 (film thickness of 18 μm), then, the obtained coated film was irradiated with solar light, and the transmittances were measured using an SPF analyzer UV-1000S (manufactured by Labsphere, Inc.) after 0 hour (before the irradiation), 3 hours and 6 hours. The measurement results are illustrated in FIG. 12.

Figure 12:
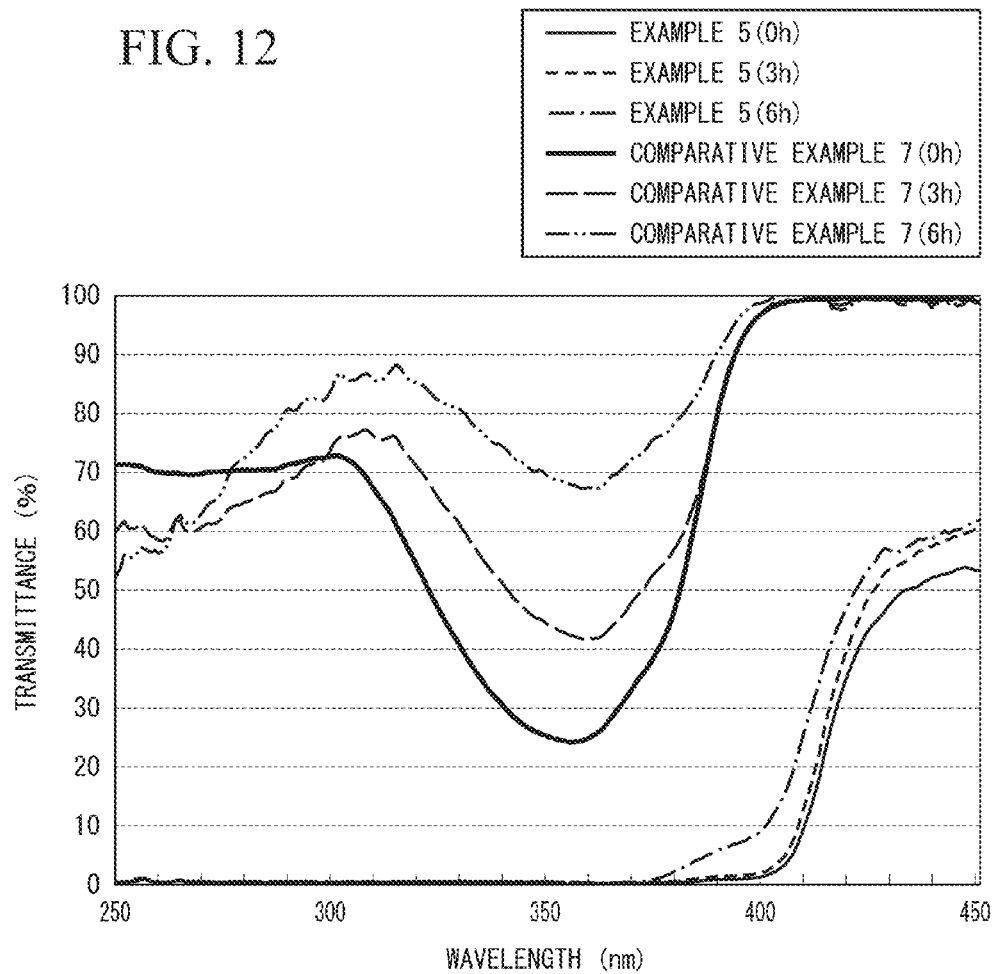
FIG. 12 is a view illustrating photostability of sunscreen agents of Example 5 and Comparative Example 7 of the invention.

From FIG. 12, it was confirmed that, compared with the sunscreen agent of Comparative Example 7 in which avobenzone was solely blended, the sunscreen agent of Example 5 had no significant change in the transmittance, and had photostability.

Example 8

Manufacturing of the Core Shell-Type Ultraviolet-Shielding Agent

A. Manufacturing of a Core Resin Particle-Dispersed Liquid Containing Zirconium Oxide Particles which Form the Core Portion Fine zirconium oxide particles RC-100 (manufactured by Daiichi Kigenso Kagaku Kogyo Co., Ltd., 40 parts by mass) having an average primary particle diameter of 0.01 μm, an ether sulfate surfactant (8 parts by mass) and methyl methacrylate (52 parts by mass) were mixed, and dispersed using a sand mill for 2 hours, thereby obtaining a monomer (MMA)-dispersed liquid including fine zirconium oxide particles dispersed in methyl methacrylate.

Next, the obtained monomer (MMA)-dispersed liquid (30.0 parts by mass), pure water (64.75 parts by mass), sodium dodecylbenzenesulfonate (0.95 parts by mass), ethylene glycol dimethacrylate (4.0 Parts by mass) and a silicone-based defoamer (0.30 parts by mass) were mixed and stirred using a homogenizer, thereby obtaining an emulsion.

Next, the obtained emulsion (80 parts by mass), pure water (20.45 parts by mass) and potassium persulfate (0.037 parts by mass) were mixed, moved to a reaction apparatus equipped with a stirrer and a thermometer, and substituted by nitrogen at room temperature (25° C.) for 1 hour. Next, the emulsion was heated and held at 65° C. for 3 hours so as to cause a polymerization reaction. Next, the reaction liquid was cooled using ice so as to stop the polymerization reaction, thereby obtaining a core resin particle-dispersed liquid containing the fine zirconium oxide particles.

B. Coating the Surfaces of the Core Resin Particles which Form the Core Portion with a Resin Including an Organic Ultraviolet Absorbent Methyl methacrylate (77 parts by mass) and a phosphate ester-type surfactant (3 parts by mass) were mixed, and, subsequently, avobenzone (Parsol (registered trademark) 1789, parts by mass) was added, thereby obtaining an organic ultraviolet absorbent-containing MMA-dissolved liquid.

Next, the organic ultraviolet absorbent-containing MMA-dissolved liquid (30 parts by mass) and a potassium persulfate-dissolved solution including potassium persulfate (0.036 parts by mass) dissolved in pure water (69.964 parts by mass) were mixed, and emulsified using a homogenizer, thereby obtaining a coated resin-emulsified liquid.

Next, the coated resin-emulsified liquid (25.5 parts by mass) and the core resin particle-dispersed liquid (74.5 parts by mass) were mixed, substituted by nitrogen at room temperature (25° C.) for 1 hour, then, heated and held at 65° C. for 3 hours, thereby causing a polymerization reaction. Next, the obtained reaction liquid was cooled using ice so as to stop the polymerization reaction, the obtained polymerized substance was washed using pure water, and then dried at 90° C. After that, the dried substance was cracked using a hammer mill, thereby obtaining a zirconium oxide-containing core shell-type ultraviolet-shielding agent of Example 8.

When the respective content rates of zirconium oxide and the organic ultraviolet absorbent in the zirconium oxide-containing core shell-type ultraviolet-shielding agent are computed based on the respective parts by mass of the coated resin-emulsified liquid and the core resin particle-dispersed liquid during the mixing, the content rate of zirconium oxide is 28% by mass, and the content rate of the organic ultraviolet absorbent is 6% by mass.

"Evaluation of the Core Shell-Type Ultraviolet-Shielding Agents"

As a result of observing a scanning electron microscopic (SEM) image of the core shell-type ultraviolet-shielding agent, the sizes of core shell-type composite particles were substantially uniform. In addition, as a result of selecting 100 particles of the core shell-type ultraviolet-shielding agent from the scanning electron microscopic (SEM) image, measuring the respective particle diameters, and computing the average particle diameter based on the particle diameters, the average particle diameter was 40 nm.

Next, the zirconium oxide-containing core shell-type ultraviolet-shielding agent (36 parts by mass), decamethyl cyclopentasiloxane (D5) SH245 (manufactured by Dow Corning Toray Co., Ltd., 75 parts by mass) and polyether-denatured silicone SH3775M (manufactured by Dow Corning Toray Co., Ltd., 9 parts by mass) were mixed, and rotated 2500 times using a sand mill so as to be dispersed for 3 hours, thereby obtaining a core shell-type ultraviolet-shielding agent-containing dispersion liquid of Example 8 containing 30% by mass of the zirconium oxide-containing core shell-type ultraviolet-shielding agent.

Next, the dispersed particle diameters of the core shell-type zirconium oxide particles in the obtained core shell-type ultraviolet-shielding agent-containing dispersion liquid were measured according to Example 1. As a result, in the cumulative volume particle size distribution, the particle diameter at the 10 volume % point (D10) was 217 nm, the particle diameter at the 50 volume % point (D50) was 302 nm, and the particle diameter at the 90 volume % point (D90) was 399 nm.

Figure 13:
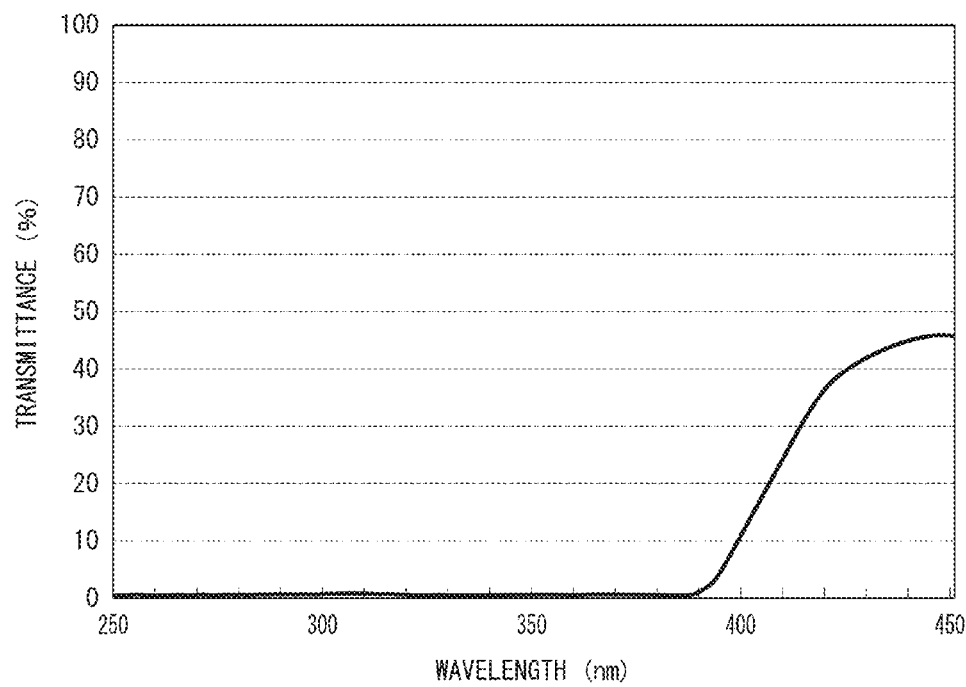
FIG. 13 is a view illustrating a spectral transmittance of a core shell-type ultraviolet-shielding agent-containing dispersion liquid of Example 8 of the invention.

The core shell-type ultraviolet-shielding agent-containing dispersion liquid was coated on a silica substrate using a bar coater so as to form a 32 μm-thick coated film, and the spectral transmittance of the coated film was measured using an SPF analyzer UV-1000S (manufactured by Labsphere, Inc.). As a result, it was confirmed that ultraviolet rays of 390 nm or less were substantially shielded. The obtained spectral transmittances are illustrated in FIG. 13.

INDUSTRIAL APPLICABILITY

According to the ultraviolet-shielding agent of the invention, it is possible to enhance the ultraviolet-shielding effect, to stabilize the quality of cosmetic preparations, and to improve the degree of freedom of the formulation as cosmetic preparations. In addition, according to the method for producing ultraviolet-shielding agents of the invention, it is possible to produce the ultraviolet-shielding agent of the invention in a favorable yield using a simple apparatus, and to reduce production costs, and therefore the invention has a large industrial value.

I claim:

1. Resin particles formed by coating a core portion with a coating layer,
   wherein the core portion is made of any one resin of an organic ultraviolet absorbent-containing resin and an inorganic particle-containing resin,
   the coating layer is made of the other resin or of both resins, and
   wherein a thickness of the coating layer is 0.01 μm to 0.5 μm.

2. The resin particles according to claim 1,
   wherein the core portion is made of the inorganic particle-containing resin, and the coating layer is made of the organic ultraviolet absorbent-containing resin.

3. The resin particles according to claim 1,
wherein a refractive index of the inorganic particles is 1.9 or more.

4. The resin particles according to claim 1,
wherein the inorganic particles are metallic oxide particles.

5. The resin particles according to claim 1,
wherein the organic ultraviolet absorbent is at least one selected from the group consisting of dibenzoylmethane-based compounds, benzophenone derivatives, para-aminobenzoic acid derivatives, methoxycinnamic acid derivatives and salicylic acid derivatives.

6. The resin particles according to claim 1,
wherein an average particle diameter of the resin particles is 0.1 μm to 5 μm.

7. The resin particles according to claim 1,
wherein the core portion is made of an inorganic particle-containing resin, and
the core portion has a spherical shape with an average particle diameter of 0.05 μm to 5.0 μm.

8. The resin particles according to claim 7,
wherein the core portion has a spherical shape with an average particle diameter of 0.05 μm to 4.8 μm.

9. The resin particles according to claim 1,
wherein the core portion is made of an organic ultraviolet absorbent-containing resin, and
the core portion has a spherical shape with an average particle diameter of 0.05 μm to 5 μm.

10. The resin particles according to claim 1,
wherein an average primary particle diameter of the inorganic particles is 0.003 μm to 0.1 μm.

11. The resin particles according to claim 1,
wherein a content rate of the organic ultraviolet absorbent in the organic ultraviolet absorbent-containing resin is 0.1% by mass to 80% by mass.

12. The resin particles according to claim 1,
wherein a content rate of the inorganic particles in the inorganic particle-containing resin is 1% by mass to 80% by mass.

13. The resin particles according to claim 1,
wherein a mass ratio of Mv:Mm of the ultraviolet absorbent to the inorganic particles is 1:9 to 5:5.

14. A resin particles-containing dispersion liquid formed by dispersing the resin particles as defined in claim 1 in a dispersion medium.

15. A cosmetic preparation comprising the resin particles as defined in claim 1 and a resin particles-containing dispersion liquid formed by dispersing said resin particles in a dispersion medium.

16. A method for producing the resin particles according to claim 1 comprising:
   a step of obtaining a resin monomer-dispersed liquid by dispersing inorganic particles in a resin monomer including a dispersant,
   a step of obtaining a resin monomer-dissolved liquid by dissolving an organic ultraviolet absorbent and a dispersant in the resin monomer,
   a step of obtaining a dispersion liquid containing a core portion made of an organic ultraviolet absorbent-containing resin or an inorganic particle-containing resin by suspending or emulsifying the resin monomer-dispersed liquid or the resin monomer-dissolved liquid in pure water including a suspension protectant, a silicone-based defoamer and a crosslinking agent, and then adding a polymerization initiator so as to carry out suspension polymerization or emulsification polymerization,
   a step of obtaining a coating resin by suspending or emulsifying the resin monomer-dispersed liquid or the resin monomer-dissolved liquid in pure water containing a polymerization initiator, and
   a step of obtaining the resin particles having a core shell structure by mixing the coating resin and the dispersion liquid containing the core portion so as to carry out suspension polymerization or emulsification polymerization.

* * * * *